(12) United States Patent
Karmon

(10) Patent No.: US 7,771,482 B1
(45) Date of Patent: Aug. 10, 2010

(54) METHOD FOR TISSUE EXPANSION AND REGENERATION USING BIORESORBABLE INFLATABLE DEVICES

(76) Inventor: Ben-Zion Karmon, 17 Yochanan Ben-Zakai, Elad (IL)

( * ) Notice: Subject to any disclaimer, the term of this patent is extended or adjusted under 35 U.S.C. 154(b) by 0 days.

(21) Appl. No.: 09/567,471

(22) Filed: May 9, 2000

(51) Int. Cl.
*A61F 2/02* (2006.01)
(52) U.S. Cl. .................................... 623/17.17; 623/908
(58) Field of Classification Search ................ 606/192, 606/57, 60, 84, 92–94; 623/23.61, 23.67, 623/23.68, 23.72, 23.74, 23.76, 17.12, 17.17, 623/17.18, 23.75, 908, 8
See application file for complete search history.

(56) References Cited

U.S. PATENT DOCUMENTS

| | | | | |
|---|---|---|---|---|
| 3,875,595 A | * | 4/1975 | Froning | 623/17.12 |
| 4,521,192 A | * | 6/1985 | Linkow | 433/173 |
| 5,146,933 A | * | 9/1992 | Boyd | 128/899 |
| 5,254,089 A | * | 10/1993 | Wang | 604/103.02 |
| 5,496,368 A | * | 3/1996 | Wiese | 623/8 |
| 5,549,676 A | * | 8/1996 | Johnson | 623/13.13 |
| 5,549,679 A | * | 8/1996 | Kuslich | 623/17.12 |
| 5,571,189 A | * | 11/1996 | Kuslich | 623/17.12 |
| 5,674,295 A | * | 10/1997 | Ray et al. | 623/17.12 |
| 5,685,716 A | * | 11/1997 | Linkow | 433/215 |
| 5,711,315 A | * | 1/1998 | Jerusalmy | 128/898 |
| 5,746,762 A | * | 5/1998 | Bass | 606/192 |
| 5,827,289 A | * | 10/1998 | Reiley et al. | 606/86 |
| 5,919,234 A | * | 7/1999 | Lemperle et al. | 623/23.72 |
| 5,977,431 A | * | 11/1999 | Knapp et al. | 623/8 |
| 6,027,744 A | * | 2/2000 | Vacanti et al. | 623/15.12 |
| 6,045,497 A | * | 4/2000 | Schweich et al. | 128/898 |
| 6,206,930 B1 | * | 3/2001 | Burg et al. | 623/23.64 |
| 6,214,012 B1 | * | 4/2001 | Karpman et al. | 606/92 |
| 6,264,695 B1 | * | 7/2001 | Stoy | 623/17.16 |

FOREIGN PATENT DOCUMENTS

| | | | |
|---|---|---|---|
| EP | 411767 | * | 2/1991 |
| WO | WO9624310 | * | 8/1996 |

* cited by examiner

*Primary Examiner*—Brian E. Pellegrino
(74) *Attorney, Agent, or Firm*—Mark M. Friedman

(57) ABSTRACT

Bioresorbable inflatable devices and tunnel incision tool and methods for treating and enlarging a tissue or an organ or a tube or a vessel or a cavity. The device is composed of a hollow expanding pouch made of a resorbable material that can be attached to a filling element. The pouch can be filled with a biocompatible materials, one or more times in few days interval, after the insertion of the device. While filling the pouch every few days the tissue expands and the filling material if it is bioactive start to function. The tunnel incision tool composed of a little blade that emerges from the surface of the tool in order to make shallow incisions in the surrounding tissue therefore enabling easy expansion of the tissue. This device and method can be used for example for: horizontal and vertical bone augmentation in the jaws and the tunnel incision tool is used to make shallow incisions in the periosteum when using the tunnel technique, sinus augmentation when the device is placed beneath the Schneiderian tissue, vessels widening if the pouch become a stent etc.

70 Claims, 14 Drawing Sheets

METHOD FOR TISSUE EXPANSION AND REGENERATION USING BIORESORBABLE INFLATABLE DEVICES

FIELD AND BACKGROUND OF THE INVENTION

The present invention relates to an improved methods and devices for treating and healing a tissue deficiency in a living human or animal body. The method and the device combine a mechanical action and a biological action.

For example, the present invention can be used for guided bone regeneration in the jaws as part of dental treatment with dental implants.

The present invention consists of an expansion device based on a bioresorbable film and a method for tissue regeneration. In order to clarify the principles of the present invention the following description will focus on two implementations: bone regeneration in the jaws preceding dental treatment with dental implants and widening a biological tube using a stent. The same principles are implemented for other tissues and other organs and other areas of the body.

Treatment of edentulous patients with osseointegrated fixtures made of titanium is a well known procedure in the art. The procedure includes installing a fixture in the alveolar bone of an at least partially edentulous jaw. Usually several months are required for proper healing after fixture installation.

After healing, an abutment is installed on the upper portion of the fixture. After several weeks, an artificial tooth may be mounted on the abutment and the procedure is complete.

Installation of implants requires sufficient alveolar bone, generally about 10 mm height and 6 mm width.

When a tooth is removed, the alveolar bone is gradually resorbed because of the absence of stimulus of ossification-inducing pressure from the teeth. As the resorption process advances, the size of the bone gets reduced, i.e. the bone on which the dental roots are positioned—the alveolar ridge start shrinking.

The absence of just one tooth can cause modifications throughout the dental arch and even prompt a possible softening (loss of insertion) which may cause the loss of other teeth. The absence of several teeth aggravates the problem. Bone loss may finally modify the patient's appearance and, depending on the loss, may make him incapable of receiving bridges, implants or even dentures.

It is then necessary to carry out several surgical operations to reconstruct the alveolar ridge of the maxilla or mandible.

Although these methods of surgical reconstruction have been successfully performed, this type of operation has had drawbacks. Certain methods have involved opening the mucoperiosteal tissue along the entire length of the atrophic alveolar ridge and then placing a bone graft material and a membrane on top of the graft and then suturing the delicate mucoperiosteal tissue back together to cover the membrane. The role of the membrane is to maintain the bone graft in its place and to prevent the mucoepithelium from growing into the graft and interfering with the process of bone regeneration. This surgical operation has had drawbacks such as:

1. Tearing of the mucoperiosteal tissue.
2. Migration of the bone graft in spite of the membrane.
3. Exposure of the membrane leading to infection and failure of the regeneration.
4. Necrosis of the mucoperiosteal tissue.
5. Insufficient enlargement of the alveolar ridge.
6. Obliteration of the buccal vestibule because of stretching of the mucoperiosteal tissue, necessitating vestibuloplasity.
7. Only lateral augmentation can be achieved bat not vertical.
8. All the hazards of a relative big operation in the mouth: bleeding, nerve damage, infection, pain etc.

Yet another technique involves creating an envelope or channel subperiosteally and then inserting the bone graft material into the channel. The bone graft can be enclosed in a resorbable casing. This procedure which is a minor surgical procedure overcome the problems of a relative big surgical procedure as described in the prior art bat has drawbacks:

1. It is difficult with this technique to place accurately the graft.
2. The surgeon is often unable to achieve the desired reconstruction of the atrophied ridge without perforating or stretching of the mucoperiosteum to the point that pressure necrosis develops.
3. Insufficient enlargement of the alveolar ridge.

In order to overcome some of these drawbacks, another small surgical procedure is done before the performance of the procedures mentioned above. In this procedure an expandable device is placed beneath the periosteum through a small incision. This device made of silicon is gradually filled with a liquid through a cannula. While this expandable device expands tension is transferred to the periosteum leading to enlargement of the periosteum. When the periosteum reached the desired dimension the expandable device is taken out and a bone graft is placed as described above, but now there is no need to stretch the mucoperiosteal tissue therefor reducing the complications.

This procedure has two significant drawbacks:

1. Two surgical procedures are needed. A small procedure for insertion of the expandable device and a big procedure for placing the bone graft and the membrane.
2. All the hazards of a relative big operation in the mouth.

Another procedure of bone augmentation preceding the placement of dental implants is called sinus lift technique or subantral augmentation technique. There are three basic methods to perform this augmentation of the maxillary sinus:

The sinus lift technique introduced by Dr. Tatum:

This procedure which is the most popular requires cutting a "trapdoor" in the lateral wall of the maxillary sinus and then lifting gently the Schneiderian membrane without tearing the membrane, then placing bone graft materials beneath the lifted membrane, then covering the "trapdoor" with a membrane and suturing. This technique has some drawbacks:

1. It is a relative big operation.
2. The technique is complicated.
3. The Schneiderian membrane can be easily torn resulting in infection of the sinus and failure of the operation.
4. The bone graft material can migrate beneath the Schneiderian membrane.

The sinus lift technique introduced by Dr. Summers:

This technique requires breaking the floor of the sinus after penetrating through the alveolar ridge beneath the sinus. The bone graft is pushed into the channel in the bone and therefore the Schneiderian membrane is elevated. This procedure has advantage over the Tatum's technique that the procedure is simpler and the operation is smaller, bat has also drawbacks:

1. The amount of augmentation is limited.
2. The Schneiderian membrane can be torn without the awareness of the surgeon resulting in filling the graft above the membrane and failure of the procedure.
3. The bone graft material can migrate beneath the Schneiderian membrane.

The sinus lift technique introduced by Dr. Jerusalmy (U.S. Pat. No. 5,711,315):

This technique includes the steps of lifting the Schneiderian membrane from the antral floor, perforating the membrane and placing graft material between the Schneiderian membrane and the antral floor. The advantage of this technique is that no bone surgery is needed, bat has drawbacks leading for very limited use of this technique:

1. The technique is complicated.
2. There is an intentional tear of the membrane that can cause infection and failure of procedure. (All the other techniques are trying to preserve the integrity of the membrane.)
3. The technique requires special equipment and skill that are not familiar to the surgeons involved in dental implantology.
4. The bone graft material can migrate beneath the Schneiderian membrane.

The present invention is unique because it is the only method and device combining together a bioresorbable barrier a graft material and an expansion device therefor avoids most of the foregoing drawbacks and permits a more simplified and effective means for bone regeneration:

1. The amount of augmentation is almost not limited.
2. The procedure is very simple.
3. There is only one surgical procedure.
4. The surgical procedure can be very small.
5. No tearing of the mucoperiosteal tissue
6. No Necrosis of the mucoperiosteal tissue
7. The risk of membrane exposure is much smaller.
8. The hazards of a big operation are avoided.
9. No obliteration of the vestibulum.
10. No migration of the graft material.
11. When used in sinus lift the chance of tearing the Schneiderian membrane is much smaller and even if the membrane is torn it is fixed automatically.
12. Vertical augmentation can be achieved.

In certain medical treatment procedures, a type of endoprosthesis device known as a stent is placed or implanted within a blood vessel for treating various problems such as stenoses, strictures, or aneurysms in the blood vessel. These devices are implanted within the vascular system to reinforce collapsing, partially occluded, weakened or abnormally dilated sections of the blood vessel. Stents may also be implanted in the ureter, urethra, bile duct, or any body vessel which has been narrowed, weakened or in any of the other ways which requires reinforcement.

A common approach for implanting stents in peripheral or coronary arteries is to first open the constricted region of the vessel via a percutaneous transluminally inserted angioplasty balloon catheter. The uninflated balloon at the tip of the catheter is advanced into the narrowed portion of the vessel lumen. The balloon is inflated so as to push the stenotic plaque outward, thereby enlarging the luminal diameter. Thereafter another catheter containing the stent is advanced to the region just enlarged by the balloon catheter and the stent is deployed. The catheter is withdrawn leaving the stent within the vessel.

The concept of implanting transluminally placed coil spring stents within an artery is not new. In one experiment in 1969, six stents were implanted in arteries of dogs. Three stents were stainless steel covered with silicone rubber and the other three stents were bare stainless steel. All three silicone coated stents occluded within 24 hours while two of the three bare stents remained open for thirty months. The stents were deployed using a pusher catheter having the same outer diameter as the stent.

In 1983, thermally expandable stents were reported, in which an alloy wire was shaped at thigh temperature into a stent configuration. Later it was straightened at room temperature into a configuration suitable for transluminal placement. Once placed within the vessel the stent was exposed to elevated temperatures to cause the alloy to return to its initial coil configuration. Canine studies of these stents, using the alloy nitinol, an alloy of nickel and titanium, demonstrated restenosis and intimal thickening 8 weeks following implant.

In 1984, self-expanding stents were described in which a device was introduced percutaneously after torsion reduction and was deployed by applying a reverse torsion in-vivo. This type of device proved to be complex and limited by a small expansion ration. Another self-expanding stent used stainless steel wire in a zig zag configuration which resulted in incomplete vascular contact and only partial healing of the device. Yet another mechanical self-expanding stent was reported where a woven multifiliment stainless steel stent was deployed by a catheter with a constricting outer sleeve. Once in place, the outer sleeve was removed allowing self-expansion of the spring stent against the vessel wall.

Thrombosis occurred in these early prototypes, especially when the vessel tapered, and at branch points and at low expansion ratios. Canine aortic implantation resulted in multiple areas of vessel-to-stent adhesion at 3 weeks following implant. The stent exhibited minimal thrombogenicity.

Balloon expandable stents were first reported as being constructed of woven stainless steel wire where the cross points were silver soldered to resist radial collapse. The stent was deployed unexpanded over a balloon catheter, and once in position the stent was expanded by the outward force of the balloon. 8 of 11 stents implanted remained open for 1 to 8 weeks. It has been observed that the amount of intimal hyperplasia to be inversely proportional to the initial vessel lumen diameter. In another version, silver soldering cross points were replaced by the use of a stainless steel tube with rows of offset slots which became diamond shaped spaces. Although neointimal hyperplasia was observed, all stents remained open in rabbit aortas for 6 months.

Placement of a stent in a blood vessel is described in Lindemann et al U.S. Pat. No. 4,878,906 where a combination of sheath covered sleeve and a balloon catheter are used to locate and place the prosthesis. No recognition is given to the problems just discussed herein.

A prosthesis system using an expandable insert is shown in Garza et al U.S. Pat. No. 4,665,918, which is typical of those devices which are implanted without any express concern for the biocompatibility of the device being inserted. One can expect many of the foregoing problems and concerns to be evidenced by this device.

One device which is shown in U.S. Pat. No. 4,768,507 to Fischell et al describes a coil spring stent on which an application of a carbon coating or a carbon coated polytetrafluoroethylene has been applied on the surface of the coil spring. Fischell et al teaches that the thrombogenic potential of the device is reduced, through a passive methodology, but does nothing to address the biological response to the implant as a foreign body. Moreover, no suggestion is made of a way to inhibit neointimal hyperplasia, which inevitably follows balloon catheter induced injury to arterial vessels.

Yasuda U.S. Pat. No. 4,994,298 employs plasma polymerization to form a thin flexible coating on stents, teaching that improved biocompatibility, such as non-thrombogenicity and tissue or blood compatibility may be improved. Again this process is a passive methodology as previously described.

Spring like stents have been inserted using a sheath or restraining element to keep the spring from expanding until It is in place. Other form of stent uses a method of expanding the stent once it is in place, such as a balloon catheter, Kreamer U.S. Pat. No. 4,740,207 describes one version of the balloon catheter version. In this patent, a semi-rigid tube which has a smaller relaxed diameter which is expanded to a larger operating diameter which is maintained by a retaining ledge on the Inside of the graft. Concern here, of course, is that the inside located ledge and other retaining means may inadvertently function to cause further blockage of the tube once it is installed. Kreamer states that the tube is held in place by friction between the outer periphery of the graft and the inner periphery of the vessel to prevent displacement of the grant once in place In the vessel. The obvious concern is that the size must be precise or the tube will expand too much or too little, either damaging the vessel or escaping from the location for which it was intended.

A number of conventional stents in order to be easily expandable have a rolled up cylinder construction. For example, U.S. Pat. No. 5,443,500 to Sigwart discloses an intravascular stent intended for implantation in a stenotic area or zone of obstruction of a blood vessel consisting of a flat sheet that is perforated to form a reticulated or lattice type structure with undeformable links and made of malleable material. The sheet is temporarily rolled up and locked in a spiral with a relatively small diameter on a deflated balloon mounted on the end of a catheter and is held in the rolled up state by a tie laced into overlapping links. Once the device is in place in the restricted area of the blood vessel to be treated and after the tie is removed, the rolled sheet is expanded to a desired diameter by inflating the balloon.

U.S. Pat. No. 5,423,885 to Williams discloses an expandable, balloon catheter delivered intravascular stent having a plurality of protrusions on its outer surface for engaging the artery walls in which it is disposed. The stent has a rolled up sheet construction, wherein apertures are formed in the stent body from the space vacated in the body by the material forming the protrusions. When the stent is expanded by the balloon catheter, the protrusions engage both the apertures and the artery walls to lock the stent into the expanded diameter.

U.S. Pat. No. 5,306,286 to Stack et al. discloses an expandable stent having a rolled up mesh construction. The stent can be reduced in diameter by a rolling motion while still having a cylindrical configuration on its outer surface for uniform engagement with a vessel wall. The rolled up, absorbable stent is mounted on either a balloon catheter, a mechanically expandable catheter, or other suitable stent delivery assembly. By expanding the distal balloon of the catheter or mechanically expandable distal end portion of the mechanically expandable catheter, the stent is expanded so as to engage the vessel wall. The stent comprises bioabsorbable porous material that reduces the likelihood of embolization and promotes tissue ingrowth in order to encapsulate the stent.

U.S. Pat. No. 5,192,307 to Wall discloses a stent-like prosthesis which is formed of plastic or sheet metal and is expandable or contractible for placement. The stent may selectively be biased towards a closed position and lockable in an open position or biased in an open position and lockable in a closed position. In the former case, the stent is put into place in its collapsed condition, then forcibly expanded by a balloon to the desired locked condition. In the latter case, the stent may be held by a pin or the like in its collapsed condition, and the pin removed to allow the stent to assume its open position. The locking function is performed by one or more hooks formed into the wall which engage complementary recesses formed in an opposing wall to mechanically interlock the rolled up sheet forming the stent.

U.S. Pat. No. 5,441,515 to Khosravi et al. discloses an intravascular stent comprising a cylindrical sheet having overlapping edges that interlock. The edges having a series of protrusions and apertures that interlock and ratchet as the stent expands to an open position to support a section of arterial wall. The stent may be expanded by a balloon catheter or it may be self-expanding. A plurality of retaining members keep the stent open, and a buckle fastening member is used in one embodiment.

There are also stents that have also therapeutic action. Often these catheters include specialized attachments for providing different treatment modalities. For example, the following references disclose catheters with attachments for administering a therapeutic agent and performing balloon therapy:

U.S. Pat. No. 4,824,436 to Wolinsky discloses a multi-lumen catheter having opposed ring balloons positionable on opposite sides of a plaque formation in a blood vessel. Inflation of the ring balloons define an isolated volume in the vessel about the plaque. Heparin is then injected into the volume between the ring to assist the body in repairing the plaque deposit. This patent also discloses a central balloon which can be employed to rupture the plaque prior to inflation of the ring balloon.

U.S. Pat. No. 4,832,688 to Sagae et al. discloses a multi-lumen catheter having an occlusion balloon positionable distally of a tear in a vessel wall. Inflating the balloon occludes the vessel and isolates at the tear. A therapeutic agent, such as heparin or thrombin, injected from the catheter into the volume reduces the risk of thrombosis or restenosis. The balloon is then deflated and moved adjacent the rupture and reinflated to repair the ruptured wall by coagulation of blood thereat.

U.S. Pat. No. 5,254,089 discloses a balloon catheter having an array of conduits disposed within the outer wall of the balloon. The conduits include apertures in the other wall for delivery of medications through the wall of the balloon into the body of a patient. This type of balloon is often referred to as a channeled balloon.

U.S. application Ser. No. 08/105,737 to Lennoxx et al., discloses catheters having spaced balloons for treating aneurysms. The inflated balloons define an isolated volume about the aneurysm. A port connects a vacuum source to evacuate the volume and draw the aneurysmal wall toward its ordinary position. Inflating a third balloon with a heated fluid to contact the aneurysmal wall effects the repair.

Therapeutic agent and balloon delivery systems must meet certain criteria. That is, the cross-sectional dimension of the catheter must be minimized to enable transit through the vessel while also having sufficient dimension to enable fluid flow to selectively inflate and deflate the balloon, guidewires to pass therein, and therapeutic agents to flow therethrough for delivery along the catheter. Catheters must also have sufficient internal rigidity to prevent collapse of the lumens while having sufficient flexibility for passage along vessels.

Stent delivery systems, as disclosed by the U.S. Pat. Nos. 5,158,548 and 5,242,399 to Lau et al. And U.S. Pat. No. 5,108,416 to Ryan et al. patents, often include a catheter supporting a compacted stent for transport in a vessel and an expansible device for expanding the stent radially to implant the stent in the vessel wall. After removal of the catheter, the expanded stent keeps the vessels from closing.

The U.S. Pat. No. 4,690,684 to McGreevy et al. patent discloses a stent formed of biologically compatible material, such a frozen blood plasma or the like. According to McGreevy et al., a stent of this type carried by a catheter may be inserted into opposed ends of a ruptured vessel to support the separated vessel walls while the ends are bonded together.

Once deployed, the heat from the bonding operation and the body eventually melt the stent and clear the vessel.

The U.S. Pat. No. 4,922,905 to Strecker, patent describes a stent and delivery system. The stent is knitted from metal or plastic filaments and has a tubular structure. The delivery system includes a balloon catheter and a coaxial sheath. The catheter supports and carries the compacted stent to a site within the body. The sheath covers the stent preventing premature deployment and facilitating transit of the stent through passages in the body. Exposure of the stent by moving the sheath axially with respect to the catheter and expansion of a balloon urges the stent into contact with the walls of the vessel. Deflation of the balloon frees it from the stent and enables withdrawal from the vessel of the delivery system.

In the U.S. Pat. No. 4,950,227 to Savin et al. patent a stent delivery system includes a catheter having an expansible distal portion, a stent carried thereon in a contracted position for expansion thereby and sleeves that overlie the end portions of the stent. The sleeves protect the vessel and the stent during transit without substantially inhibiting deployment of the stent.

In accordance with the Anderson patent a stent delivery system includes a dissolvable material that impregnates a self-expanding stent in a compacted form. In one embodiment the removal of a sheath exposes the stent to body heat and liquids so that the material dissolves and the stent expands into a deployed position.

Stent delivery systems used in such procedures generally include catheters with selectively expansible devices to deliver and expand a contracted "stent" or restraints that can be removed to allow a self-expanding stent to assure an enlarged or expanded configuration. Stents are known and have a variety of forms and applications. For example, stents serve as prostheses and graft carriers in percutaneous angioplasty. Stents used as an endoprothesis and graft carriers to which the present invention relates usually comprise radially expansible tubular structures for implant into the tissue surrounding vessels to maintain their patency.

Like the previously described therapeutic agent and balloon therapy systems, stent delivery systems must conform to several important criteria. First, it is important to minimize the transverse dimension of the delivery system, so the stent must be capable of compaction against a delivery device, such as a catheter. Second, the delivery system must facilitate the deployment of the stent once located in a vessel. Third, the stent delivery system must easily disengage from the stent after the stent is deployed. Fourth, the procedure for removing the delivery system from the body must be straightforward. Fifth, the delivery system must operate reliably.

It has been found that the administration of therapeutic agents with a stent can reduce the risks of thrombosis or stenosis associated with stents. Stents administered along with seed cells, such as endothelial cells derived from adipose tissue, can accelerate the reformation of an afflicted area. Likewise, tears or other vessel damage associated with balloon angioplasty can be reduced by a deployed stent used in combination with a therapeutic agent.

When both therapeutic agent and stent therapies are required, a physician generally (1) steers a guidewire to the treatment locus, (2) guides a catheter over the guidewire, (3) operates the catheter to provide the first stage of treatment, (4) inserts an exchange guidewire to the guidewire, (5) withdraws the catheter, (6) guides a second catheter over the guidewire, and (7) operates the second catheter to provide the second stage of treatment. After this, the physician withdraws the guidewire, if not previously removed, and the catheter from the body of the patient.

U.S. Pat. No. 5,439,446 to Barry a stent delivery system that incorporates a drug delivery system in the catheter. This device permits the surgeon to use one catheter to deliver both the stent and the therapeutic agent at a selected site in the patient's body.

Other references disclose the use of stents that release therapeutic agents associated with a deployed stent over time. For example U.S. Pat. No. 5,234,457 to Andersen commonly assigned as this invention discloses stents impregnated with a gelatin that enables the release of the stent. It is suggested that the gelatin could entrain a therapeutic agent that dispenses as the gelatin dissolves.

These references thus provide the ability to deliver stents and therapeutic agents to an afflicted site within a patient's body and even enables the dispersion of the therapeutic agent from the stent over time. However, if additional therapeutic agent is needed at the site another catheter must be inserted to deliver the therapeutic agent or by generally introducing the additional therapeutic agent to the vessel such as by injection in the case of a blood vessel or by bathing the esophagus for example.

In some cases where a slow release of the therapeutic agent is desired, as by the release of a therapeutic agent entrained in a gelatin or other hydrophilic or hydrophobic polymers on a stent. Once the therapeutic agent was delivered, replenishment required one of two procedures. In one, a new stent was inserted to be adjacent the old stent. Sometimes this reduced the effectiveness of the therapeutic agent, particularly when the area of treatment was displaced from the second stent. An alternative that overcame that problem was substituting a new stent for the old stent. It is true that percutaneous transluminal procedures and other procedures involving the insertion of stents into the body have improved in recent years. Likewise the reduction in the size of the instruments inserted into the patient reduces the risk of damage. However, it is still a fact that each insertion and extraction risks further damage to afflicted areas and damage to otherwise unaffected areas through which the instruments pass and can add to patient trauma. Moreover, insertion and withdrawal of additional instruments in sequence increases the time of the physician, staff, and medical facility, and the cost of multiple instruments. Thus, reducing the number of instruments and the overall size of the instruments necessarily inserted and withdrawn from a patient, the steps required by the processes, and the overall size of each of the instruments is generally preferred.

U.S. Pat. No. 5,857,998 to Barry enables replenishment of a reservoir in the stent with therapeutic materials.

None of the prior art is enabling the widening of the vessel without temporarily blocking the passage through the vessel.

None of the prior art enables gradually widening of the vessel over some days therefor limiting the risk of rupture.

None of the prior art enables safely widening the vessel beyond the final desired diameter to compensate for future restenosis.

In none of the prior art the balloon is the stent

None of the prior art has all the other properties of an ideal stent bat only some of them.

The other ideal properties of a stent are:
1. The insertion of the stent is done in one phase. There is no need for a first balloon to widen the constriction.
2. The stent is the balloon therefor no need of withdrawal of the balloon.
3. The stent is biocompatible.
4. The stent is bioresorbable.
5. The amount of widening is determined and monitored while doing the procedure, without concern for the precise size of the stent being employed or the size of the vessel being treated or repaired.
6. The stent can be used to close ruptures of the vessel.
7. The stent is well attached to the vessel's walls.
8. The stent has therapeutic material on its outer surface facing the walls of the vessel.
9. The stent has therapeutic material on its inner surface facing the lumen of the vessel.
10. The stent can release therapeutic materials from a reservoir.
11. The reservoir can be replenished.
12. The stent can produce rapid endothelialization with the least mount of intimal hyperplasia.
13. The stent is strongly attached to the vessel's walls therefor the risk of embolization is small
14. The stent is easily inserted to the vessel therefore the risk of damaging the vessel is minimized.
15. The stent can adapt itself to bent shape of a vessel and furcations
16. The stent in which problems associated with restenosis, thrombosis, infection calcification and/or fibrosis after implantation may be avoided.
17. The procedure is simple and short.
18. The widening can be changed after the procedure is over.
19. The stent is mechanically strong and can resist crush.
20. The stent is flexible and compliant.
21. risk of embolization is small.

Therefore, it is an object of this invention to provide a method and apparatus that has some or all of these properties.

SUMMARY OF THE INVENTION

The present invention provides a method and device by which inserting a biocompatible material into the body and at same time mechanically enlarging the surrounding of the device. The biocompatible material can be a bioactive material like a drug or inert material.

The device is made of a pouch that can be filled preferably through a filling element with the biocompatible material. The pouch is made fully or partially of a bioresorbable material and it acts like a balloon that expands as it is filled with the biocompatible material.

The pouch is filled one or more times every few days till the desired enlargement is reached. While the pouch expands it conducts tensile forces to the surrounding tissues which reacts in proliferation and enlargement. At the same time more biocompatible materials are added. After the desired enlargement is reached the filling element can be pull out if necessary. There is no need to take out the pouch because it is made of bioresorbable materials. The end result is a new or enlarge compartment in the body filled with a biocompatible material.

The insertion of the device can be through a small incision to a tunnel so all the process is done with almost no surgery. Through this incision the tunnel incision tool can be inserted before the insertion of the device. The tunnel incision tool makes shallow incision in the surrounding tissue of the tunnel. These incisions allow initial expansion of the tissue and easy insertion of the device.

There are many possible implementations of the device and method depending on several factors:
1. The place the device is inserted into.
2. The filling material.
3. The shape of the pouch.
4. The kind of filling element that is in use.
5. The kind of material the pouch is made of.

The device and method can be therefore used for selective regeneration of more or less specialized tissues, for example, membranes demarcating body cavities and/or separating different tissues and organs from each other, as well as, for selective regeneration of different tissues within the organs, or the organs themselves in relation to the surrounding tissues or nerves. Examples of membranes are the periosteum, the membranes of the brain and the peritoneal membrane; while examples of organs are the liver, the throat, the ventricle, the kidney, the heart and the pancreas. Also, muscle tissue tendons, fat tissue, vessels, ducts, and tubes should be possible to regenerate with this device and method.

The device and method are particularly useful for plastic surgery, dental implantology and in cardiac surgery. In plastic surgery it can be used for soft tissue enlargement like lips and breasts and for facial bones enlargement. In dental implantology it can be used for horizontal and vertical augmentation of the alveolar ridge when the pouch is placed beneath the periosteum and for sinus augmentation when the pouch is placed beneath the Schneiderian membrane preceding the placement of dental implants. In cardiac surgery it can be used as a bioresorbable stent for vessel widening.

Other objects and features of the present invention will become apparent in the following detailed description when taken in connection with the accompanying drawings which disclose one embodiment of the invention. It is to be understood that the drawings are designed for the purpose of illustration only and are not intended as a definition of the limits of the invention.

Thus, according to the teachings of the present invention there is provided, a method for expanding, stretching or displacing living tissue comprising: (a) inserting into the tissue an inflatable element made at least in part from bio-dissipative material; (b) introducing into the inflatable element a quantity of a biocompatible filling material so as to displace the tissue; and (c) leaving at least part of the inflatable element in place for a period sufficient to allow the bio-dissipative material to disperse.

According to a further feature of the present invention, the introducing is performed in a plurality of stages separated by at least a number of hours, each stage incrementally stretching the tissue.

According to a further feature of the present invention, the biocompatible filling material includes a bio-active material.

According to a further feature of the present invention, the biocompatible filling material includes material for promoting the growth of at least one type of tissue.

According to a further feature of the present invention, the inflatable element is located beneath the Schneiderian membrane of the maxillary sinus or of the nose.

According to a further feature of the present invention, the inserting is performed such that the inflatable element is located substantially at a bone-soft tissue interface, the biocompatible filling material including material for promoting the growth of bone such that, subsequent to dispersal of the inflatable element, the biocompatible filling material promotes extension of the bone beyond the initial bone-soft tissue interface.

According to a further feature of the present invention, the material for promoting the growth of bone includes at least one material selected from the group made up of: an autograft, an allograft, a xenograft, an alloplast, a cytokine, a hormone, a growth factor, a physiologically acceptable drug, a biological modifier, a protein, an antigen, a cell chemotaxis stimulator material, a material inducing osteogenesis, an osteoinduction material, and an osteoconduction material.

According to a further feature of the present invention, the inflatable element includes a guided bone regeneration membrane located so as to be adjacent to the soft tissue.

According to a further feature of the present invention, the inflatable element is configured to have a first region which exhibits a first mean time to dispersion and a second region which exhibits a second mean time to dispersion longer than the first mean time to dispersion.

According to a further feature of the present invention, the inflatable element is formed at least in part from a stretchable material.

According to a further feature of the present invention, the inflatable element is formed from more than one type of material.

According to a further feature of the present invention, the inflatable element is configured to have a first portion with a first stiffness and a second portion with a second stiffness differing from the first stiffness.

According to a further feature of the present invention, the inflatable element is formed at least in part from a material which serves as a selective barrier configured to allow at least a first material to traverse the barrier while preventing passage of at least a second material.

According to a further feature of the present invention, the inflatable element is formed at least in part from a self-expanding material.

According to a further feature of the present invention, the biocompatible filling material includes a self-expanding material.

According to a further feature of the present invention, the introducing is performed via a filling conduit partially inserted into the tissue.

According to a further feature of the present invention, the filling conduit is formed at least partially from non-bio-dissipative material.

According to a further feature of the present invention, the filling conduit includes a sealing means for sealing the filling conduit after the introducing of the biocompatible filling material.

According to a further feature of the present invention, disinfecting material is introduced into the filling conduit after the introducing of the biocompatible filling material.

According to a further feature of the present invention, the filling conduit is implemented as a bone implant.

According to a further feature of the present invention, the filling conduit is formed with at least one fixation feature.

According to a further feature of the present invention, the introducing is by temporarily puncturing the inflatable element with a needle inserted through the tissue, the inflatable element being configured to be self-sealing on removal of the needle.

According to a further feature of the present invention, prior to inserting the inflatable element, a tunnel is formed into the tissue for insertion of the inflatable element.

According to a further feature of the present invention, prior to inserting the inflatable element, a plurality of shallow, elongated incisions are formed in the tissue adjacent to the tunnel so as to facilitate stretching of the tissue.

According to a further feature of the present invention, the shallow elongated incisions are formed manually by moving an elongated tool with at least one laterally projecting blade in a reciprocating motion within the tunnel.

According to a further feature of the present invention, the elongated tool is configured to produce incisions of depth no greater than about 2 mm.

According to a further feature of the present invention, the elongated tool is configured to produce incisions of depth between about 0.1 mm and about 1 mm.

According to a further feature of the present invention, the inflatable element is configured to apply outward force on a substantially cylindrical living tissue without completely obstructing a flow path which passes within the substantially cylindrical living tissue.

According to a further feature of the present invention, the inflatable element is configured as a double-walled sleeve.

There is also provided according to the teachings of the present invention, a device for expanding, stretching or displacing living tissue comprising: (a) an inflatable element for insertion into the tissue, the inflatable element being made at least in part from bio-dissipative material; and (b) means for introducing into the inflatable element a quantity of a biocompatible filling material so as to displace the tissue.

According to a further feature of the present invention, the inflatable element is configured to have a first region which exhibits a first mean time to dispersion and a second region which exhibits a second mean time to dispersion longer than the first mean time to dispersion.

According to a further feature of the present invention, the inflatable element includes a guided bone regeneration membrane.

According to a further feature of the present invention, the inflatable element is formed from a plurality of types of material.

According to a further feature of the present invention, the inflatable element is configured to have a first portion with a first stiffness and a second portion with a second stiffness differing from the first stiffness.

According to a further feature of the present invention, the inflatable element is formed at least in part from a material which serves as a selective barrier configured to allow at least a first material to traverse the barrier while preventing passage of at least a second material.

According to a further feature of the present invention, the inflatable element is formed at least in part from a self-expanding material.

According to a further feature of the present invention, the inflatable element is formed at least in part from a stretchable material.

According to a further feature of the present invention, the means for inflating includes a filling conduit configured for inserting into the tissue so as to be accessible from outside the tissue, the filling conduit being formed with at least one fixation feature configured to allow fixation of the conduit relative to the tissue.

According to a further feature of the present invention, the filling conduit is formed at least in part from non-bio-dissipative material.

According to a further feature of the present invention, the filling conduit includes a sealing means.

According to a further feature of the present invention, the filling conduit includes a chamber for receiving disinfectant material.

According to a further feature of the present invention, the filling conduit is implemented as a bone implant.

According to a further feature of the present invention, the means for introducing includes a hollow needle configured to pierce part of the inflatable element for filling, the inflatable element being configured to reseal itself after withdrawal of the needle.

According to a further feature of the present invention, the inflatable element is configured to apply outward force on a substantially cylindrical living tissue without completely obstructing a flow path which passes within the substantially cylindrical living tissue.

According to a further feature of the present invention, the inflatable element is configured as a double-walled sleeve.

There is also provided according to the teachings of the present invention, an elongated tool for forming shallow elongated incisions in living tissue adjacent to a tunnel formed through the tissue so as to facilitate stretching of the tissue, the tool comprising: (a) a handle; (b) an elongated shaft associated with the handle, the elongated shaft having a direction of elongation, a maximum transverse dimension measured perpendicular to the direction of elongation and a length measured parallel to the direction of elongation, wherein the maximum transverse dimension is at least about 3 mm and wherein the length is at least five times the maximum transverse dimension; and (c) at least one blade projecting from the elongated shaft and configured to form incisions of depth no greater than 2 mm in adjacent tissue when the tool is inserted within the tunnel and moved parallel to the direction of elongation.

According to a further feature of the present invention, the length is at least about ten times the maximum transverse dimension.

According to a further feature of the present invention, the maximum transverse dimension is between about 5 mm and about 10 mm.

According to a further feature of the present invention, the at least one blade is configured to form incisions of depth between about 0.1 mm and about 1 mm.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
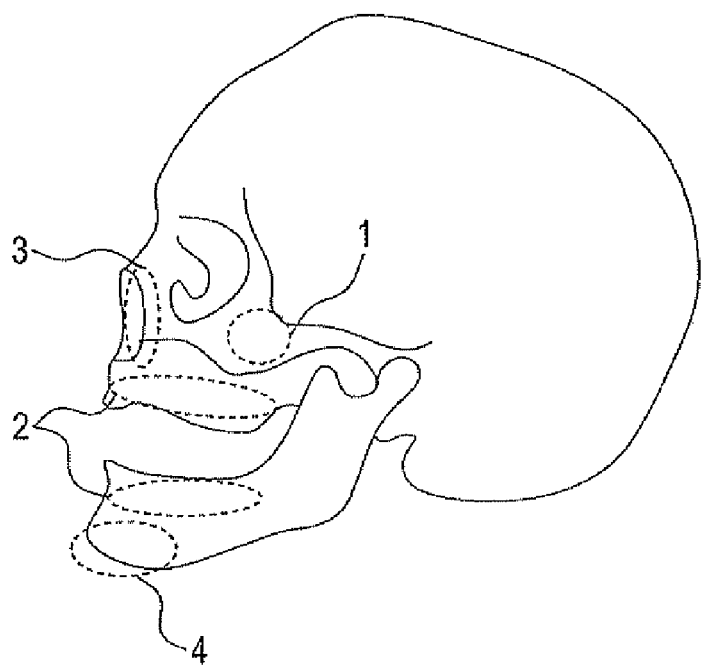
FIG. 1 is a side view illustrating the skull of a human being and indicating general areas in which the skull bone structure is often augmented.

As mentioned further above there are many implementations of the invention in different tissues and organs. The following description will focus on embodiments in two fields in order to understand the principles of the device and method. The first is bone augmentation in the jaws and the second is vessel widening using a bioresorbable stent. The same principles should be used in other tissues and organs.

Before turning to the features of the present invention in more detail, it will be useful to clarify certain terminology as will be used herein in the description and claims. Specifically, it should be noted that the present invention is useful in a wide range of applications in which living tissue is to be expanded, stretched or displaced. The term "living tissue" is used herein to refer to any living tissue including, but not limited to, an organ, tube, vessel, cavity, or membrane, and interfaces between any two or more of the above. Where used within a single type of tissue, the typical application of the present invention is for expanding the tissue. When used at a tissue interface, the invention is typically used to displace one of the types of tissue, in many cases for the purpose of expanding/extending the other tissue. The invention may also be used to increase the inner dimensions of tubes, vessels or cavities within the body.

In another matter of terminology there are many types of body canals, blood vessels, ducts, tubes and other body passages, and the term "vessel" is meant to include all such passages. In a further matter of terminology, it is noted that a large number of different types of materials are known which may be inserted within the body during a surgical procedure and which later dissipate, thereby avoiding the need for a separate surgical procedure for their removal. Such materials are properly referred to, depending upon the mechanism by which the material dissipates, as "bioresorbable", "bioabsorbabie" or "biodegradable". Despite the differences between these different classes of materials, the aforementioned terminology is widely used interchangeably by medical professionals. Accordingly, and for conciseness of presentation, only one of these terms will generally be used in the following description, without implying the exclusion of the other classes of materials. Additionally, the phrase "bio-dissipative material" is used herein in the description and claims to refer generically to any and all materials which dissipate without requiring surgical removal, independent of which mechanisms such as dissolution, degradation, absorption and excretion take place. The actual choice of which type of materials to use may readily be made by one ordinarily skilled in the art, and is not generally essential to the present invention.

Finally with respect to terminology, reference will be made to a biocompatible filling material used to fill the inflatable elements of the present invention. It should be noted that this filling material may assume a wide range of compositions and consistencies, so long as the biocompatible material may be forced into the inflatable element. Thus, possible consistencies for the filling material include, but are not limited to, consistencies described as watery, viscous, gelatinous, moldable, waxen, particulate, and suspensions or mixtures combining any of the above.

Turning now in detail to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates the zygomatic 1, alveolar ridge 2, paranasal 3, and submental 4 bone areas on one side of the face of the skull of a human being. These areas are often augmented.

Figure 2:
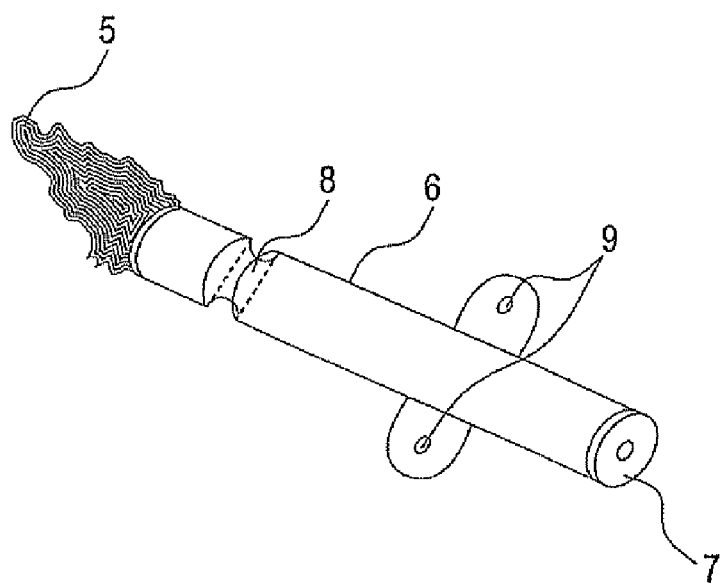
FIG. 2 is a perspective view illustrating the novel device used in accordance with the invention to receive and contain bone augmentation material. in this preferred embodiment the filling element is a cannula.

FIG. 2, illustrates the novel device embodying the present invention for use in bone reconstruction and, in particular, for augmentation of atrophic alveolar ridges 2. The device is composed of resorbable pouch 5. The pouch can be made from autograft, allograft, xenograft and alloplast and combination thereof. Preferably, pouch is made of conventionally available polyglycolic acid (PGA) mesh, a high-molecular-weight linear polymer made by the ring opening polymerization of the purified glycolide monomer, although other suitable materials might be used e.g. polyglactin 910, i.e. polyglycolide co-galactide. In addition, collagen or PDS (another absorbable suture material) or cellulose might possibly also be used as a pouch material. The pouch should be porous towards the bone to allow bone tissue ingrowth and block epithelial tissue ingrowth. The pouch should be resorbable to prevent a chronic foreign body reaction. The pouch should not allow the filling material to get out of the pouch and should stand out pressure.

The pouch 5 is connected to a conduit in the shape of a cannula 6. The conduit can be also catheter, valve, bone implant, syringe and combination thereof. Bone implant can be hollow bone implant, slotted bone implant, threaded implant, cylinder implant, smooth surface implant, titanium plasma sprayed implant, hydroxyapatite coated implant, acid etched surface implant, sand blasted surface implant, S.L.A. surface implant, ceramic implant, zirconium implant and any combination thereof.

The conduit is made of a biocompatible material and can be made from more then one type of material bioresorbable or non-bioresorbable. Preferably the cannula is made of commercially pure titanium or titanium alloy used in the dental implant industry. The cannula is connected to the pouch in one side and in the other side it can be filled and closed with a screw 7 as a sealing component. Sealing components can be also a valve, a clamping element, a knot and combination thereof. The conduit can have variable shapes, dimensions, cross section and elasticity The cannula 6 has preferably fixating components in order to prevent the cannula from moving, get out and cause uncomfortable filling to the patient. The a fixation component can be selected from the group consisting of hook, hole for sutures, slot, thread, bulge, screw, change in dimension, irregularity and any combination thereof.

Figure 3:
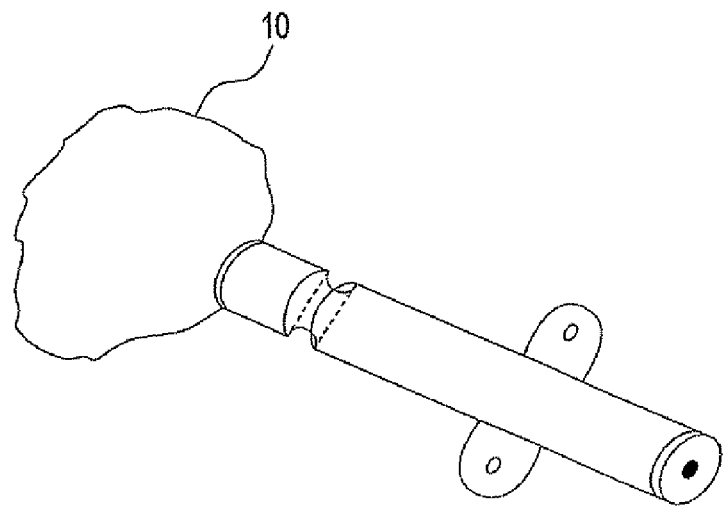
FIG. 3 is a perspective view illustrating the device of FIG. 2. After it was filled with bone augmenting material.

In this preferred embodiment there are three fixating component. One fixating component is a slot 8 that is near the pouch and inserted into the body. After the tissue heals around the slot it prevent the cannula from getting out easily. The other two fixating components are holes for sutures 9 that are near the sealing screw 7 and not inserted into the body. After the insertion of the device the pouch can be filled with bone augmenting material causing the wrinkled and compressed pouch 5 to expands and become a filled pouch 10 in FIG. 3.

Figure 4:
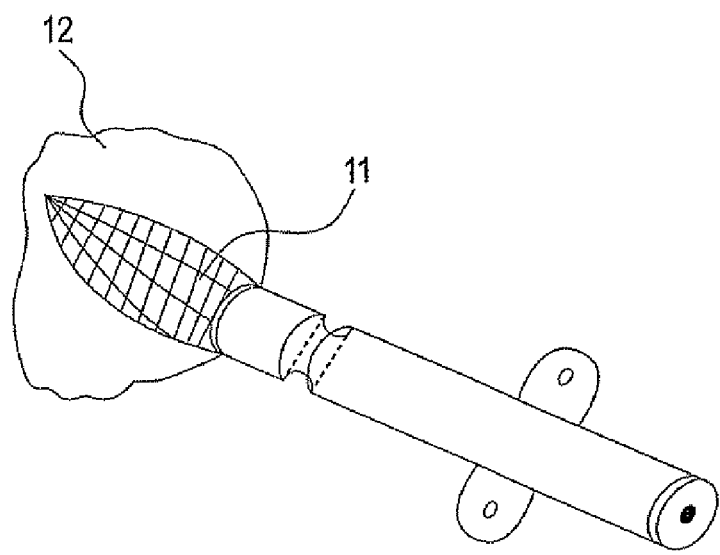
FIG. 4 is a bottom view illustrating the device of FIG. 3.

The pouch can be made of more the one type of material. Preferably the pouch is composed of two types of resorbable materials illustrated in FIG. 4. One type that is rapidly resorbed 11 and allows bone ingrowth and the second type 12 that is slowly resorbed and prevent the ingrowth of epithelial tissue. When inserting the pouch the rapidly resorbed material 11 should face the bone.

The slowly resorbed material 12 can be also not resorbable material like ePTFE if in this case the gums are going to be open when placing the dental implants and then the not resorbable material can be taken out.

The pouch can include also self expanding components. Materials include, either alone or in combination, metals or metal alloys, polymers, carbon and ceramics. Exemplary metallic members include stainless steel, titanium, tantalum, shape-memory materials such as nickel-titanium alloy (NiTi) (Compounds using NiTi are manufactured under the marks NITINOL™ and ELASTINITE™ and are available from several sources), Elgiloy (trade name) and NP35N (trade designation), which can provide desired degree of springiness, malleability and/or response to temperature changes. Exemplary polymers include polyurethanes, silicon rubbers, polyether sulfones, fluoroelastomers, polyimides, polycarbonates, polyethylens, polylactic acid, polyglycolic acid, polyacrylates, and the like and combinations and copolymers thereof which provide a variety of abilities to bioabsorb or biodegrade or to be totally inert. The pouch can include springs and coils that are compressed before insertion and can include stretchable and elastic materials for example polyurethanes like polycarbonate urethane.

In another preferred embodiment the pouch can include materials with different degree of stiffness. The material facing the bone can be less stiff the material facing the gums.

The pouch can have variable shapes and the volumes according to the use. For example to reconstruct the entire jaw the pouch will be elongated in C-shape and filling element will be attached in the middle.

In another preferred embodiment the pouch also includes a selective barrier that permits transfer of some cells and materials and prevents the transfer of other cells and materials. Therefor allowing bone forming cells and blood to get inside the pouch and block the entrance of connective tissue cells. This barrier can also permit the release of medication mixed with the filling material without letting the filling material to leak. This barrier should be adopted for its specific use for example to have little holes sized according to the medicine to be released.

Figure 5:
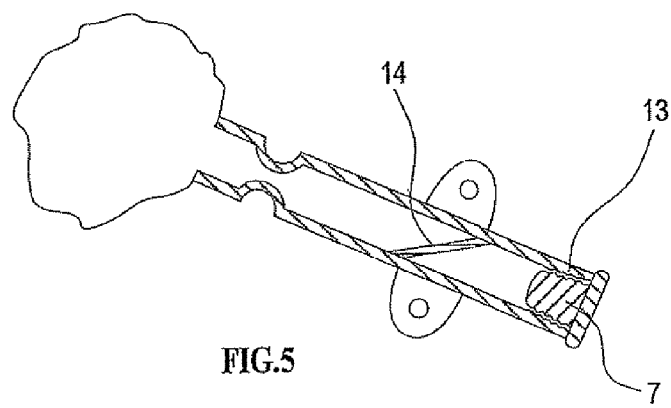
FIG. 5 is a sectional view of the device of FIG. 2.
Figure 6A:
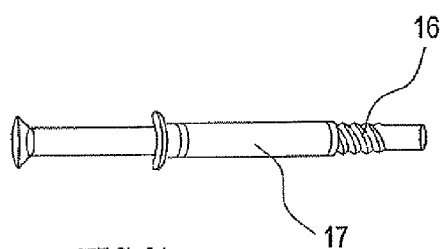
FIG. 6A is a perspective view illustrating a filling instrument containing bone augmenting material.

FIG. 5 illustrates a sectional view of the device revealing internal threads 13 for the sealing screw 7 and another sealing component preferably a valve 14 that is open while filling the pouch and is closed otherwise. The chamber 15 between the two sealing components the screw 7 and the valve 14 is preferably filled with biocompatible antiseptic material like chlorhexedine gel or calcium-hydroxide. The antiseptic material should be washed out before filling and put again when the cannula is closed. FIG. 6A illustrates a preferably filling syringe to be used with the device. The syringe has threads 16 on its tip that mach the internal threads 13 in the cannula used for the screw. The syringe is preferably filled with bone augmenting material 17 in gelatinous consistency or suspension. The filling material can be an autograft, an allograft, a xenograft, an alloplast, a cytokine, a hormone, a growth factor, a physiologically acceptable drug, a biological modifier, a protein, an antigen, a cell chemotaxis stimulator material, a material inducing osteogenesis, an osteoinduction material, an osteoconduction material, a bioactive material, a bioresorbable material, a bioabsorbable material, a biodegradable material and any combination thereof. The filling material can be augmenting bone material available in the market like hydroxyapatite, bovine mineral (i.e. Bio-Oss available from Geistlich, Swiss), demineralized freezed dried bone, synthetic materials like PLA (i.e. PhisioGraft from Atrix). The filling material can be also fully or partially not bioresorbable if the procedure is done only for aesthetic reason and implants are not going to be inserted, for example crystal hydroxyapetit.

The filling material can include therapeutic materials and can include self expanding materials from the list mentioned above. Many of the bone augmenting material has the tendency to expand when getting wet by hydration.

Figure 6B:
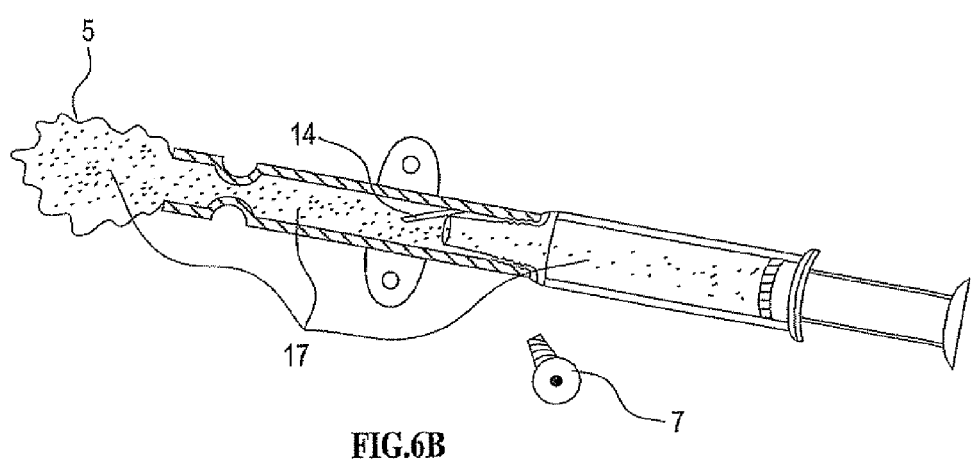
FIG. 6B is a sectional view illustrating the filling instrument of FIG. 6A connected to and filling the device of FIG. 2.

In order to fill the device the screw 7 is screwed out and the syringe is screwed in illustrated in FIG. 6B. While inserting the syringe into the cannula and screwing the syringe the valve 14 is opened allowing the filling of the pouch 5 with the filling material 17. When the syringe is taken out the valve is closed preventing the filling material to leak out.

The pouch can be filled directly without a conduit if the pouch has a region prepared to be perforated by a needle of a syringe and has self sealing mechanism on removal of the needle as described in U.S. Pat. No. 5,695,338 to Robert.

Figure 7A:
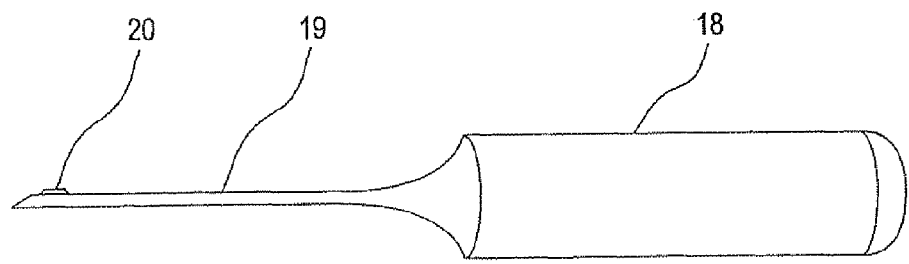
FIG. 7A is a side view illustrating the tunnel incision tool.
Figure 7B:
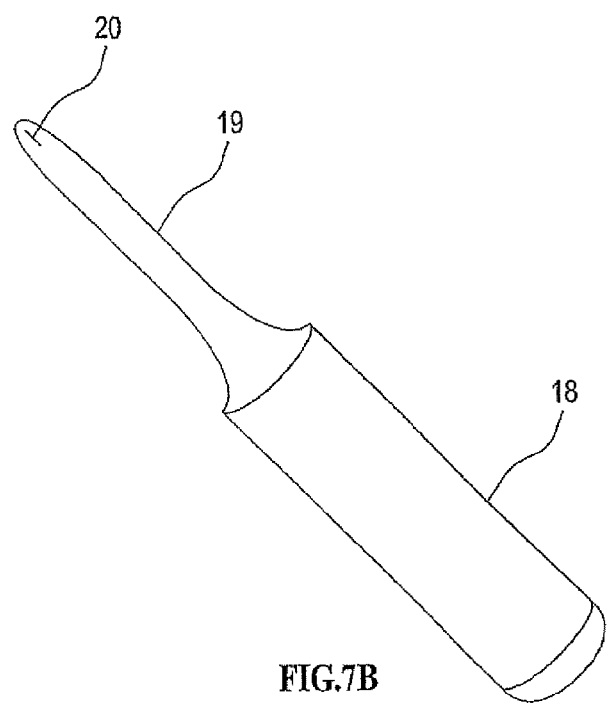
FIG. 7B is a top view illustrating the tunnel incision tool.

FIG. 7A and FIG. 7B illustrates a side view and a top view of the novel tunnel incision tool. The tool consists of a handle 18 connected to a shank 19. From the surface of the shank 19 a little blade 20 is emerging. There can be more the one blade and the can be arranged in different angles. The tool can be made from different types of materials like stainless steel and to enable replacing of the blades or plastic for one use only. The shank can be made from elastic materials. In another preferred embodiment the height of the blade can be regulated.

The shape size length and surface texture of the handle and the shank and the blade and the angle between them can be changed according to the region in the mouth. While inserting the shank 19 into a tunnel the blade 20 is making shallow incision to the tissue touching the blade. Because the height of the blade 20 is very small and the blade is surrounded by the surface of the shank, deep incisions and perforation of the tissue is avoided. If the tissue is very thin the use of the tunnel incision tool is not recommended.

Figure 8A:
FIG. 8A is a front perspective view of a patient's mouth prepared for the insertion of the device with incision on one side of the lower jaw.
Figure 8B:
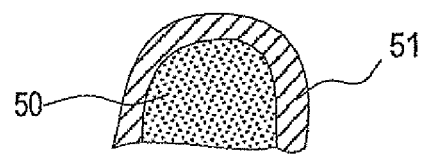
FIG. 8B is a sectional view of the alveolar ridge of FIG. 8A.
Figure 9:
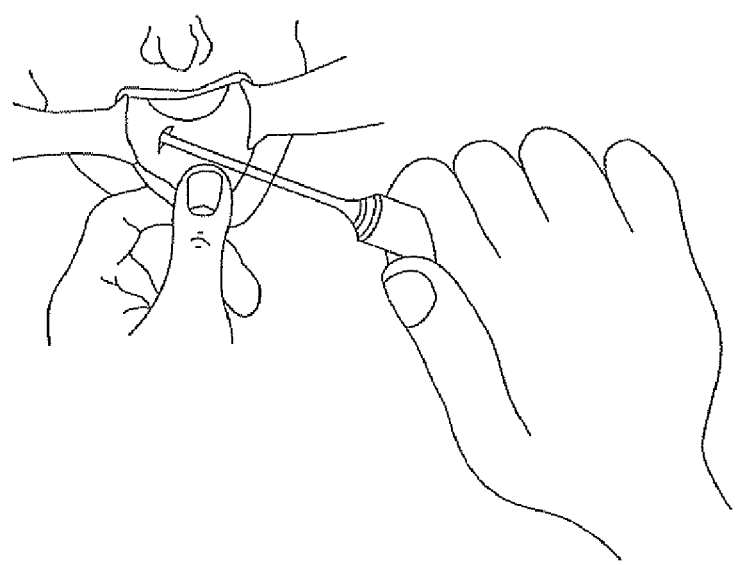
FIG. 9 is a front perspective view of a patient's mouth while inserting the tunnel incision tool into the subperiosteal tunnel.
Figure 10:
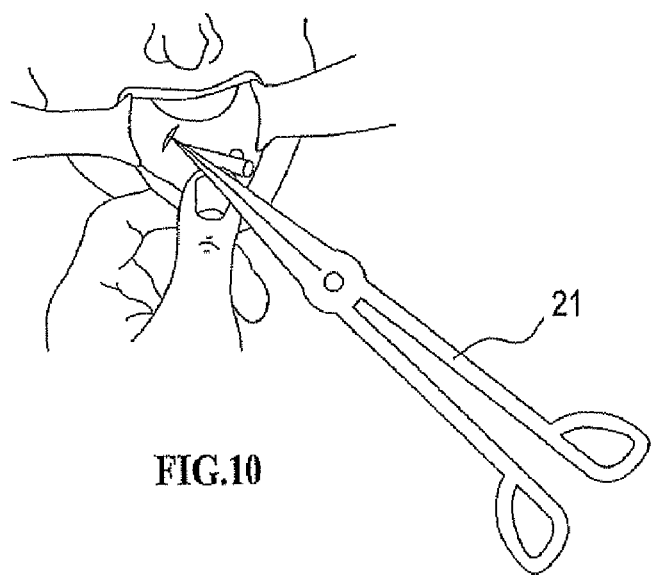
FIG. 10 is a front perspective view of a patient's mouth while inserting the pouch of the device subperiosteally using an insertion tool.
Figure 11A:
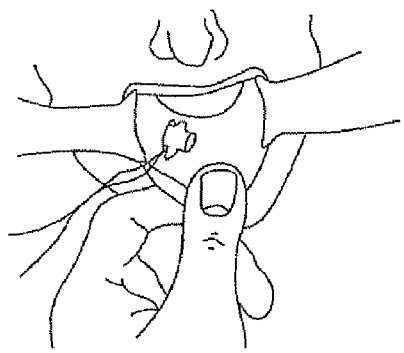
FIG. 11A is a front perspective view of a patient's mouth after the insertion of the pouch of the device beneath the gums and suturing the incision and fixating the protruding cannula.
Figure 11B:
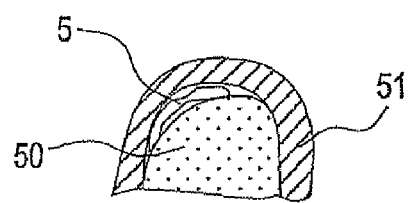
FIG. 11B is a sectional view of the alveolar ridge of FIG. 11A after the insertion of the device.
Figure 12A:
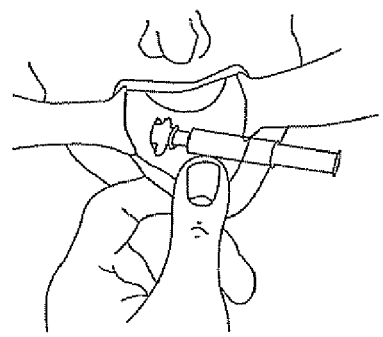
FIG. 12A is a front perspective view of a patient's mouth several days after the insertion of the device. The filling instrument is connected to the cannula and filling the pouch.
Figure 12B:
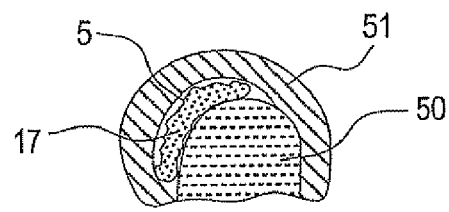
FIG. 12B is a sectional view of the alveolar ridge of FIG. 12A after some filling of the device.
Figure 13A:
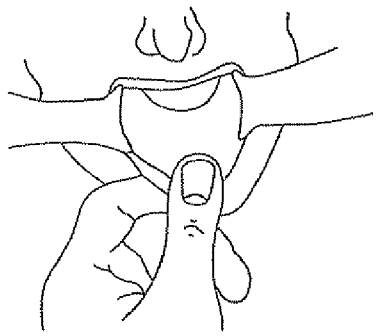
FIG. 13A is a front perspective view of a patient's mouth at the end of the filling process and removal of the cannula.
Figure 13B:
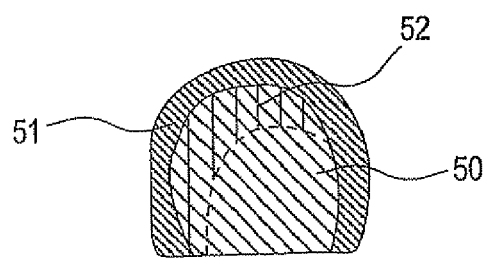
FIG. 13B is a sectional view of the alveolar ridge of FIG. 13A at the end of the procedure.

The preferred method for using the device of FIG. 2 is illustrated in the following views. The purpose of the following preferred embodiment is to augment the bone on the buccal and occlusal aspects of the alveolar ridge on the right side of the mandible. FIG. 8A illustrates a small incision done in the buccal aspect of the alveolar ridge on the right side of the mandible. FIG. 8B illustrates a sectional view of the alveolar ridge showing the atrophic alveolar ridge 50 covered by the mucoperiosteal tissue 51. After the incision is done, touching the bone, a small perioseatal elevator is inserted through the incision subperioseatally separating the periost from the bone and creating a subperiosteal tunnel. After the tunnel is prepared, the novel tunnel incision tool illustrated in FIG. 7 is inserted and taken out several times in different areas of the tunnel as illustrated in FIG. 9, creating shallow incisions in the periosteum without perforating the mucoperisteal tissue. The incisions in the periosteum enable easy expansion of the mucoperiosteal tissue without large tension. After the tunnel is made a bone file is inserted to the tunnel scratching the cortical bone to cause bleeding in order to induce bone repair cascade and to take out any granular tissue. After the tunnel and the bone are prepared the novel device illustrated in FIG. 2 is inserted using an insertion tool 21 through the incision occupying the tunnel as illustrated in FIG. 10. The device is inserted so the part of the pouch that resorbs first is facing the bone. The slot 8 of the device is inserted into the tunnel and the holes 9 for sutures are left outside the tunnel. After the insertion of the device the device is fixate by sutures using the holes 9 for sutures as illustrated in FIG. 11. FIG. 11B illustrates a sectional view of the alveolar ridge showing the atrophic alveolar ridge 50 covered by the mucoperiosteal tissue 51 and the pouch 5 of the device in between. After the device is correctly placed and fixate it can be filled. The filling can be done immediately after the insertion or after several days. It is recommended to do some initial filling immediately after the insertion to verify the correct function of the device. FIG. 12A illustrates the filling process, a filling syringe as illustrated in FIGS. 6A and 6B is screwed to the device without moving the device and filling the device with bone augmenting material until some bleaching of the tissue above the pouch 5 is seen. It is important not to fill too much in each filling session and not to cause too much tension to the tissue. The filling process can be done once or several times in 2-3 days intervals until the desired enlargement is reached. FIG. 12B illustrates a sectional view of the alveolar ridge showing the atrophic alveolar ridge 50 covered by the mucoperiosteal tissue 51 and the pouch 5 of the device partially filled with bone augmenting material 17 in between. The mucoperiosteal tissue is expanded. When the time of the resorption of the part of the pouch connected to the cannula is reached the cannula is taken out and the orifice is closed. The end result is augmented ridge seen in FIG. 13A. FIG. 13B illustrates a sectional view of the new alveolar ridge showing the previous atrophic alveolar ridge 50 and the new bone 52 covered by the expanded mucoperiosteal tissue 51. After 6-9 months it is possible to proceed toward the insertion of dental implants in the augmented ridge.

The foregoing procedure has been described in terms of the mandible. Of course, the same procedure can also be applied to reconstruction of the maxilla and other bones and for other tissues in the body.

For example in another preferred embodiment a similar device can be inserted into the lips or breast filled with material that stimulate fat tissue regeneration or connective tissue regeneration resulting in enlargement of these organs.

Another preferred embodiment can use a device that the filling element for example the cannula is made of two parts one is external made of nonresorbable material and the second is internal made of bioresorbable material. The border between the two is preferably the slot. In this device it is easy to take the nonresorbable part out by twisting the cannula and leaving the bioresorbable inside the body.

Figure 14:
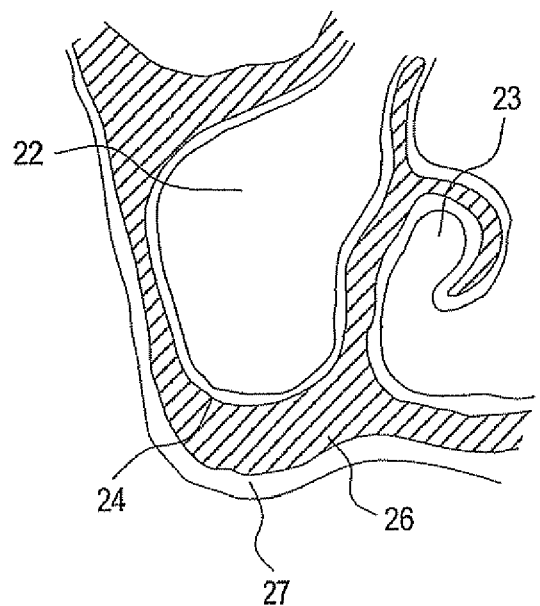
FIG. 14 is a sectional view of the maxillary sinus.

Another preferred embodiment of the device and method is bone augmentation of the maxillary sinus called also sinus lift. This procedure is done when the alveolar ridge beneath the maxillary sinus is too short—less then 8 mm height. FIG. 14 illustrates a sectional view of such a sinus 22 near the nasal cavity 23. The floor of the sinus 24 is lined with a delicate membrane called the Schneiderian membrane 25. Beneath the floor of the sinus 24 is the short alveolar ridge 26 covered by the gums 27.

Figure 15:
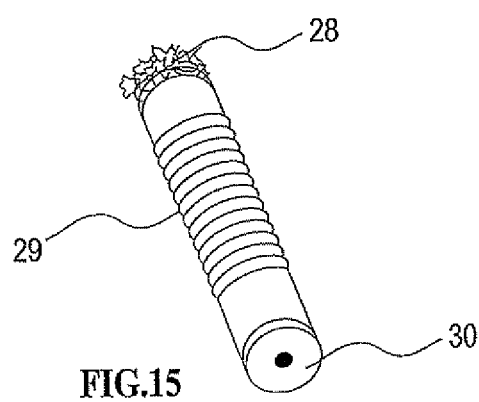
FIG. 15 is a perspective view illustrating the novel device used in accordance with the invention to receive and contain bone augmentation material. In this preferred embodiment the filling element is a hollow bone implant.
Figure 16:
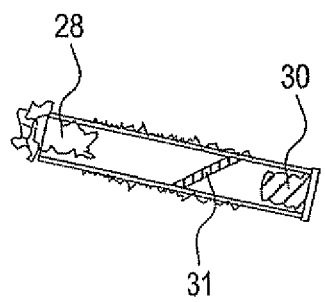
FIG. 16 is a sectional view of the device of FIG. 15.

FIG. 15 is illustrating a preferred device appropriate for this preferred embodiment. The pouch 28 of the device is preferably made of collagen and the cannula is preferably a hollow dental implant 29. FIG. 16 illustrates a sectional view of the device of FIG. 15. The device has preferably two sealing components a screw 30 and a valve 31. The pouch 28 can be fully or partially packed inside the hollow implant 29.

Figure 17:
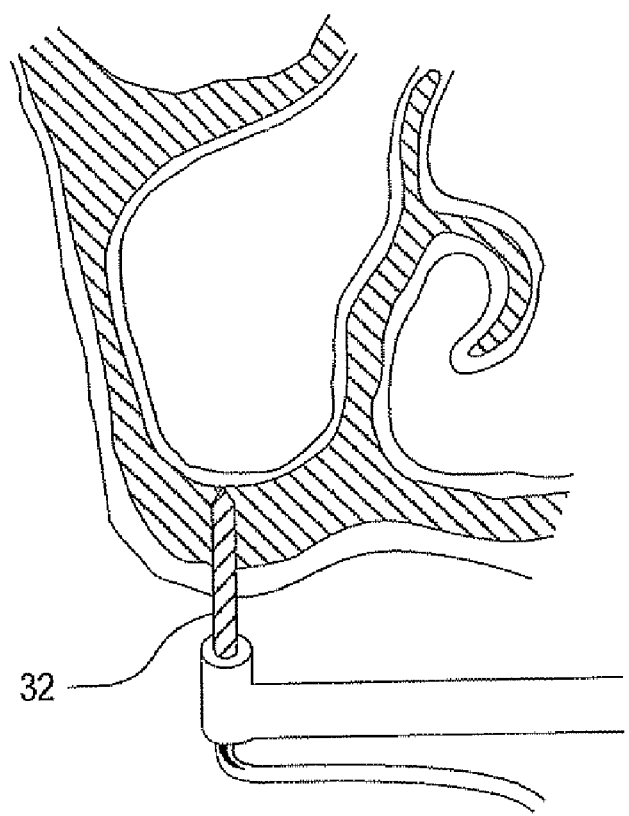
FIG. 17 is a schematic illustration of drilling to reach the floor of the sinus.
Figure 18:
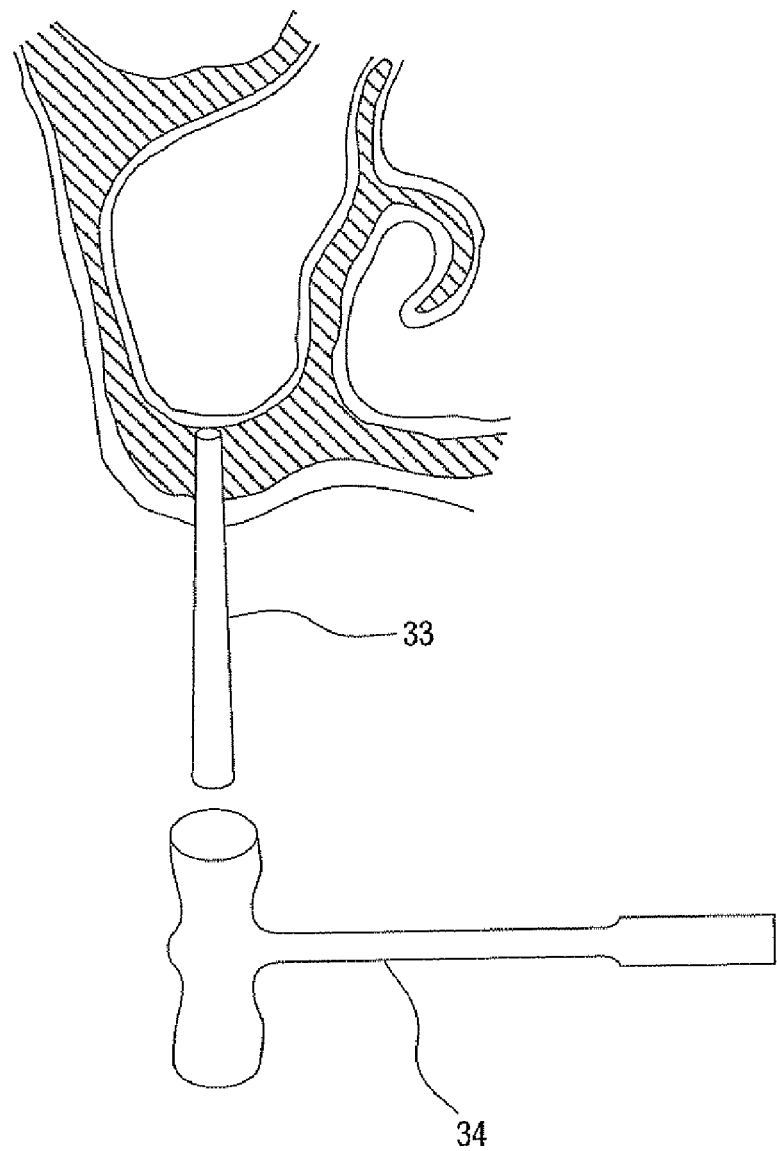
FIG. 18 is a schematic illustration of breaking the floor of the sinus using an osteom.
Figure 19:
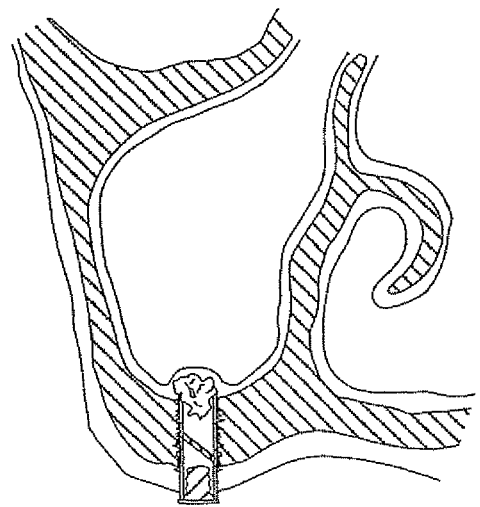
FIG. 19 is a sectional view of the sinus after placement of the device of FIG. 15 beneath the Schneiderian membrane.
Figure 20A:
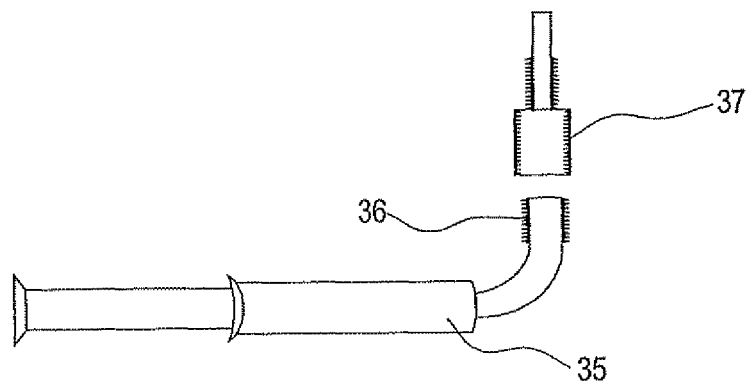
FIG. 20A is a sectional view illustrating a filling syringe filled with bone augmenting material for filling the device in sinus lift procedure. The syringe is composed of two parts.
Figure 20B:
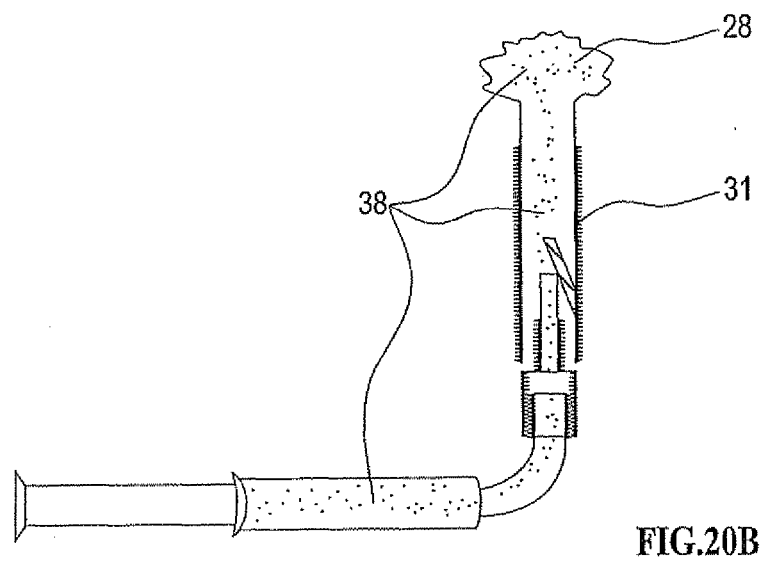
FIG. 20B is sectional view illustrating the filling syringe of FIG. 20A connected to and filling the device of FIG. 15.

The preferred method for using the device of FIG. 15 is illustrated in the following views. The purpose of the following preferred embodiment is to augment the bone above the floor of the sinus 24 and beneath the Schneiderian membrane 25. The first step is drilling using a phisio-dispenser through the alveolar ridge and the gums until touching the floor of the sinus as illustrated in FIG. 17. Preferably several drills 32 in ascending diameters are to be used as is the technique in the osteotomy for dental implants. It is also possible to raise a small mucoperiosteal flap before the drilling. It is also possible to do the osteotomy with osteoms instead of drilling. After the floor of the sinus is reached inserting an osteom 33 through the osteotomy and using a mallet 34 to gently brake the floor of the sinus crating a green stick fracture as illustrated in FIG. 18. After the break of the floor, the device of FIG. 15 is inserted through the osteotomy and raising the Schneiderian membrane approximately 1 mm as illustrated in FIG. 19. If the hollow implant is a thread implant as the implant of FIG. 15 it is screwed in place, if the implant is cylindrical it is inserted using the mallet. The diameter of the last drill should fit the diameter of the implant and the length of the implant should fit the height of the alveolar ridge beneath the maxillary sinus. In this preferred embodiment there is no need for fixating components because the hollow implant is fixated by the bone. After the fixation of the device it can be filled with bone augmenting material preferably using the syringe illustrated in FIG. 20A and FIG. 20B. The syringe is composed of two parts the body 35 and extension 36 of the syringe form one part and the tip of the syringe 37 is the second part. The tip 37 is screwed on the extension 36. After the parts of the syringe are assembled together the syringe is brought to the hollow implant, taking the screw of the implant out and screwing the tip 37 into the hollow implant while holding the body of the syringe 35. When the tip is screwed inside the hollow implant it opens the valve 31 allowing the bone augmenting material 38 to fill the pouch 28 as illustrated in FIG. 20B. The purpose of this design of the syringe is to allow access to the posterior part of the maxilla.

Figure 21:
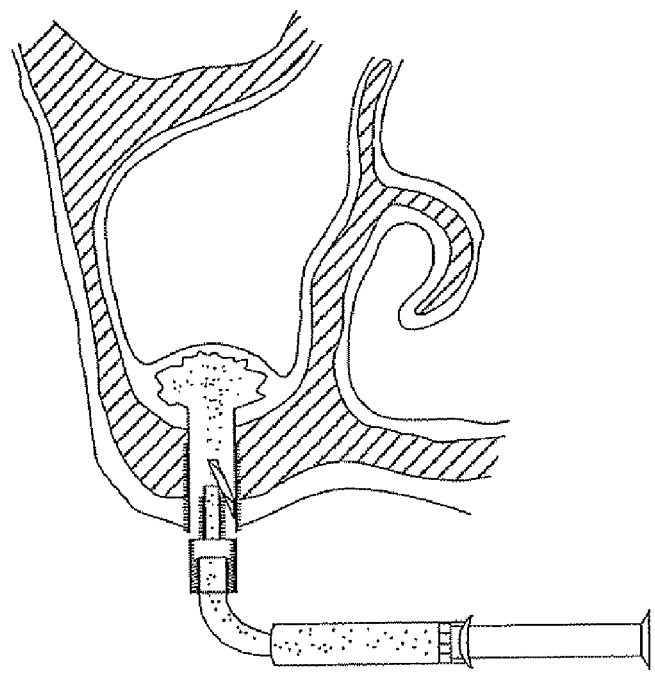
FIG. 21 is a sectional view of the sinus after filling the pouch of the device of FIG. 15 with bone augmenting material and raising the Schneiderian membrane
Figure 22:
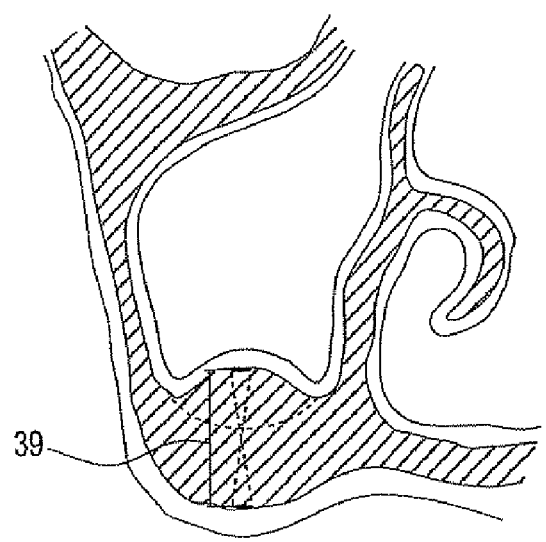
FIG. 22 is a sectional view of the sinus after the removal of the hollow bone implant.

While the pouch is filled the Schneiderian membrane is raised as illustrated in FIG. 21. Even if the membrane is torn in the procedure of inserting the implant or filling the pouch the tear is automatically closed by the pouch material. The end result of the procedure is illustrated in FIG. 22 the alveolar ridge is higher 39 compared to the alveolar ridge before the procedure. The previous floor of the sinus is marked by the dotted line.

Figure 23:
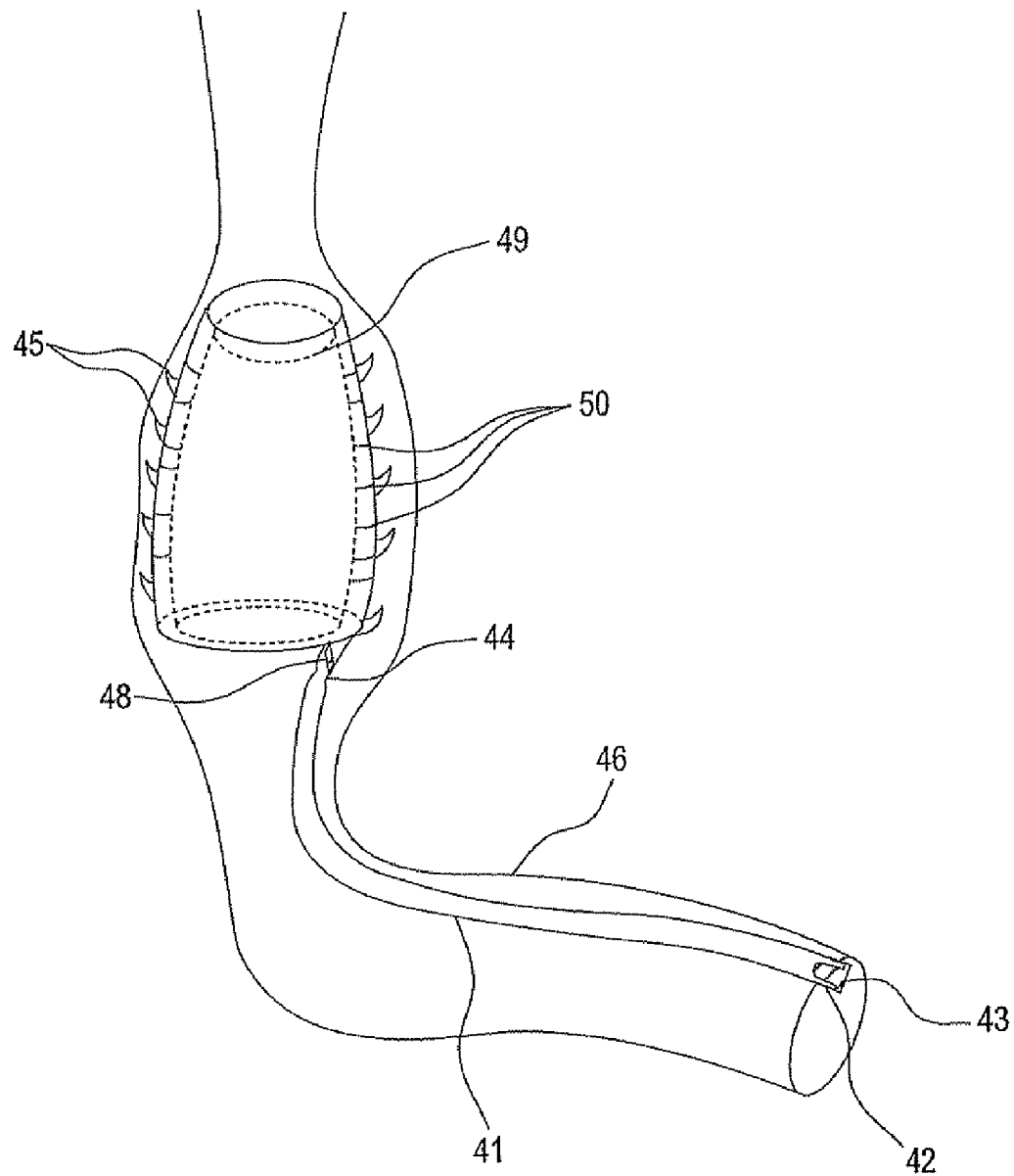
FIG. 23 is a perspective view illustrating the novel device used in accordance with the invention to widen a vessel. In this preferred embodiment the filling element is a catheter and the pouch is in the shape of a double wall sleeve.

Another preferred embodiment of the device and method is the widening of tubes like fallopian tubes, urethra, intestines, trachea, vessels etc. Without blocking the passage through the tube. The preferred device and method for this purpose is illustrated in FIG. 23. In this preferred embodiment the pouch is the shape of double wall sleeve 49. There are little cords 50 connecting the inner wall to the outer wall.

Figure 24:
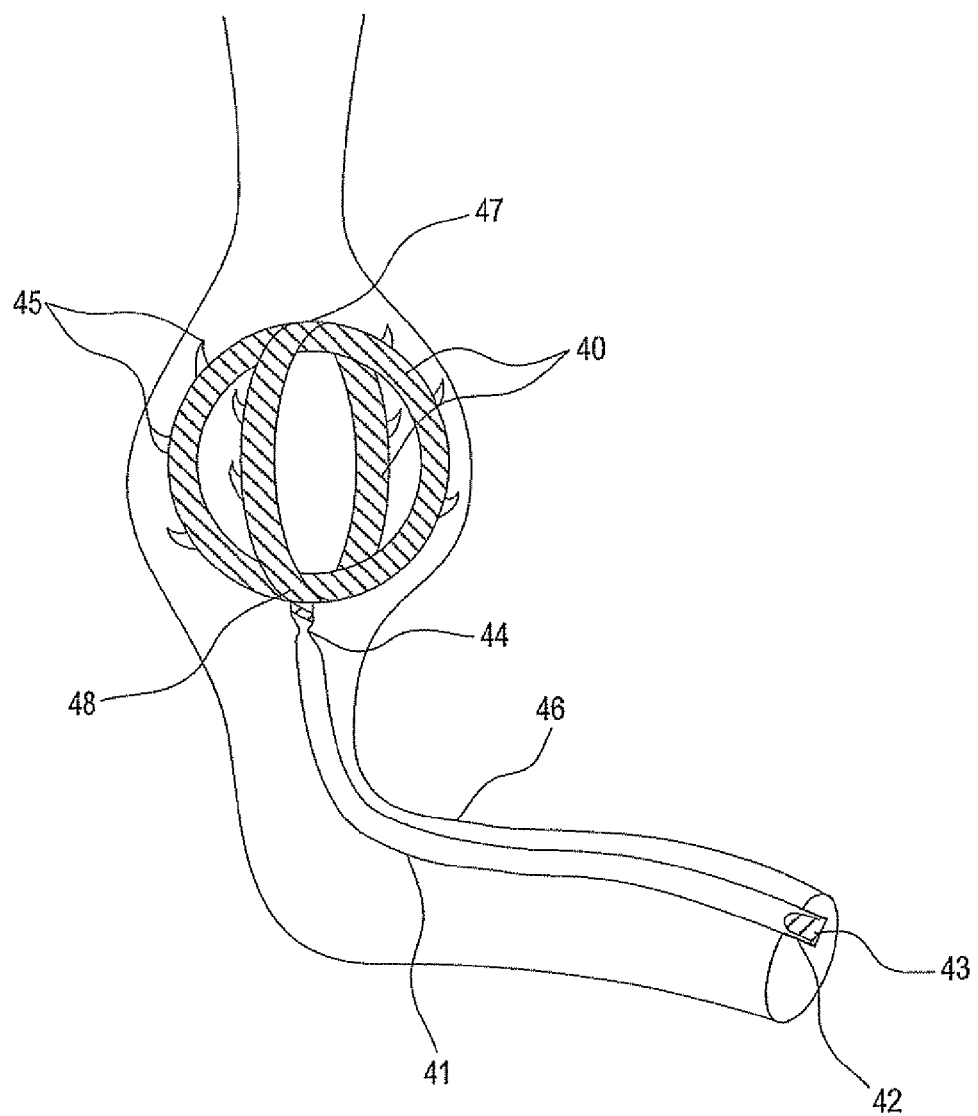
FIG. 24 is a perspective view illustrating the novel device used in accordance with the invention to widen a vessel. In this preferred embodiment the filling element is a catheter and the pouch is in the shape of two connected perpendicular tubes.

In another preferred device illustrated in FIG. 24 the pouch is in the shape of two circular tubes that are connected 40. This configuration is particularly useful where an intravenous filter function is required.

This pouch is connected to a catheter 41 (filling conduit) made of bioresorbable material that has a bioresorbable valve 48. The external part of the catheter 42 is made of nonresorbable material and has a sealing component a screw 43. There is a slot 44 in the catheter 41 which is the braking point for taking the catheter out after finishing all the filling of the balloon. The device can be made from different kinds of bioabsorbable materials. For instance, a polymer from the linear aliphatic family, such as poly (lactic acid) PLA, poly (glycolic acid) PGA or polycaprolactone, and their associated copolymers, may be employed polyglactin (PGA-PLA), polydioxanone, polyglyconate (copolymer of trimethilene carbonate and glycolide). Biodegradable polymers such as polyorthoester, polyanhydride, polydioxanone and polyhydroxybutyrate may be also employed. By using PLA+PGA as bioresorbable polymer fibers, and by changing the mixing ratio, the half value period for resorption may be freely controlled within a time period of from weeks to several months. The stiffness of the stent can be controlled as well. It is therefor possible to made the device from several types of materials for example the outer wall from one type, the inner wall from another type and the conduit from another material.

The outer surface of the pouch have arrow heads 45 made of a harder bioresorbable material (like PLA) on the external surface for stabilizing the pouch to the walls of the vessel 46 to be widened. There are many ways to configure the shape of these stabilizing elements some of them are described in U.S. Pat. Nos. 5,593,434 and 5,423,885 to Williams. The basic idea is that the outer surface is not flat and smooth but has holes or protrusions.

Briefly, and in general terms, when the stent is to be deployed in a coronary artery the stent is attached to a catheter prepared for PTCA angioplasty and using a guidewire and tracked by a fluoroscope the stent is percutaneously introduced into the vessel until the stent is positioned at the desired location.

To facilitate the placement of the stent of the present invention, the stent may be impregnated with a radiopaque material, making it opaque, and therefore visible, to X-rays. Suitable radiopaque materials include iodine based materials and solutions thereof, and barium salts, including materials containing iodipamide (sold commercially under the trade name Cholografin) and iopanic acid (sold under the trade name Telepaque).

After reaching the desired location starting filling the pouch with a biocompatible liquid. When the pouch of FIG. 23 starts to expand it forms a tube. The inner wall of the pouch facing the bloodstream the outer wall facing the walls of the vessel. Between the inner wall an the outer wall of the pouch the filling material is present. The little cords 50 ensures that the inner wall is connected to the outer wall and not collapsing to occlude the vessel In this case when the pouch is inflated the vessel is widened and vessel is not occluded. When the pouch of FIG. 24 starts to expand it forms two perpendicular tubes that are widening the vessel. The joining points of the two tubes are reinforced with a harder bioresorbable material (like PLA) in the shape of a cross 47. These crosses assure that the two tubes are aligned perpendicular to each other. When the pouch expands it forms two perpendicular tubes so the vessel is widened bat the vessel is not occluded because fluid can pass between the perpendicular tubes. The inflated pouch of FIG. 23 and FIG. 24 is now the stent The pouch can be inflated several times in some days interval if necessary until reaching the desired widening. It is recommended to widen the vessel more then final desired widening to compensate for future restenosis.

When the stent has been expanded to widen the vessel the stent is affixed in place by the arrow heads 45 engaging the walls of the artery, including the endothelium layer. It is believed that the endothelium layer of the artery will grow into the stent over a short period of time (in 7 to 21 days), to further retain the stent in place. The stent eventually will dissolve and endothelium layer growth into the stent and ensures that pieces of the stent will not discharge into the bloodstream and cause embolism as the stent is dissolved.

After the desired widening is reached the external portion 41, 42 is taken out leaving the bioresorbable device inside the tube. The device eventually will be resorbed therefor the chances for chronic inflammation or excess hypertrophy of the vessel are small and consequently reconstriction of the vessel may be inhibited.

This type of stent is flexible and compliant and crush resistant. This type of stent can be very small before inflation therefor can pass through small vessels without damaging the vessels while insertion and can adapt itself to the bent shape of the vessel of to furcations.

In another embodiment the filling material can be self expanding. It can expands by hydration for example. The stent itself can have self expanding materials.

In another preferred embodiment of the device and method the stent can be attached to a catheter with plurality of lumens therein. These lumens terminates in plurality of conduits that open to the outer wall of the stent. This configuration can enable the delivery of bioactive materials like medications. An example of this idea can be seen in U.S. Pat. No. 5,254,089 to Wang.

In a similar embodiment the stent can be made of two tubular balloons. The first one as described for expanding the device and the second circumferentially disposed over the first one for delivery of medications. The outer wall of the second balloon should have little holes for the release of the bioactive materials. Each balloon is connected to a different conduit.

In another preferred embodiment the outer wall of the balloon is made of selective barrier and filled with at least two materials. The first material is for expanding the pouch and the second is a bioactive material. The expanding material should be biocompatible liquid with high molecular weight. The outer wall barrier should enables only the release of the bioactive materials. The holes in the membrane should fit the bioactive material. In this embodiment the same conduit allows the expanding of the pouch and the administration of the bioactive materials. In this embodiment it is possible to add bioactive materials for a long time after the introduction of the stent with no surgical procedure.

Bioactive materials can be also incorporated into the material of the pouch or can be impregnated with a therapeutic agent to provide localized drug delivery, As the pouch is resorbed the material are released. Moreover, encapsulating the active agent in a dissolving material such as albumin or various polymers which would effect a continuing release of the active agent proximate the irregular wall portion during the patency of the encapsulating agent. Examples of such polymers would include pluronics gels, citric acid cycle polymers, such as polylactic acid polyglycolic acid and derivatives thereof, polyanhydrides, polyphosphazenes, polysaccarides, such as alginic acid, chitin and derivatives thereof, collagen and derivatives thereof, and glicosaminoglicans such as hyaluronic acid and derivatives thereof.

In another embodiment the release of bioactive materials can be electrically monitored or monitored by temperature as described in U.S. Pat. No. 5,857,998 to Barry for treating aneurismal wall.

The bioactive materials for all these embodiments may be selected from the group of heparin and derivative thereof, antiplatelet agents such as PPACK, iloprost, integrelin, chimeric antibodies such as c7E3 urokinase, t-PA, hirudin, prostacyclenes and analog thereof, antithrombogenic agents, thrombus lysing agents, steroids, ibuprofen, antimicrobials, antibiotics, tissue plasma activators, rifamicin, monoclonal antibodies, snake venom protein by-products, antifibrosis agents, hyaluronate, cyclosporine, genetic therapies including antisense oligonucleotides and various gene constructs, antiproliferatives such as angiopeptin, chemotherapeutic agents such as paolitaxel, antioxidants such as probucol, vasorelaxants such as nitroglycerin and papverine or ones with multiple effects such as nitric oxide and mixtures of these bioactive substances.

In this preferred embodiment of FIG. 24 there is only one step of insertion. It is true that percutaneous transluminal procedures and other procedures involving the insertion of stents into the body have improved in recent years. Likewise the reduction in the size of the instruments inserted into the patient reduces the risk of damage. However, it is still a fact that each insertion and extraction risks further damage to afflicted areas and damage to otherwise unaffected areas through which the instruments pass and can add to patient trauma. Moreover, insertion and withdrawal of additional instruments in sequence increases the time of the physician, staff, and medical facility, and the cost of multiple of multiple instruments.

The device can be used also for the quick closure of a rupture in a vessel.

In another embodiment the stent can be modified by heating.

Although the present invention has been described and illustrated in the context of certain preferred embodiments, it will be understood that modifications may be made without departing from the spirit of the invention.

What is claimed is:

1. A method for treating bone within a living body comprising:
(a) creating a hole in a periosteal tissue of a bone for insertion of an expandable portion of a container, said bone having a bone surface, said bone surface being touched by a covering tissue of said bone, said covering tissue is selected from the group consisting of periosteal tissue and Schneiderian membrane;
(b) prior to inserting said expandable portion of said container, forming a subperiosteal tunnel between said bone and said periosteal tissue, for insertion of said expandable portion of said container,
(c) inserting through said hole between said bone surface and said covering tissue said expandable portion of said container, the external surface of said expandable portion of said container having at least one region which includes at least one opening which is open sufficiently to allow penetration of bone tissue and blood vessels, said expandable portion of said container includes an area which is less penetrable to tissue than said region;

(d) expanding said expandable portion of said container so that said opening is facing said bone surface and at least part of said area is facing said covering tissue, said expanding of said expandable portion of said container is displacing said area to displace said covering tissue from said bone surface so the distance between said covering tissue to said bone surface is increased to allow bone regeneration between said covering tissue and said bone surface.

2. The method of claim 1, wherein said expanding is performed in a plurality of stages separated by at least a number of hours, each stage incrementally stretching at least one of the periosteal tissues of said bone.

3. The method of claim 1, wherein said area of said container includes a guided bone regeneration membrane located so as to be adjacent to said periosteal tissue.

4. The method of claim 1, wherein said region exhibits a first mean time to dispersion and said area exhibits a second mean time to dispersion longer than said first mean time to dispersion.

5. The method of claim 1, wherein said expandable portion of said container is configured so part of the region facing said periosteal tissue is made from a biocompatible metal and another part of the region facing said periosteal tissue is made from a slowly dissipative bio-dissipative material.

6. The method of claim 1, further comprising, prior to inserting said expandable portion of said container peeling said periosteal tissue from said bone.

7. The method of claim 1, wherein said periosteal tissue is the mucoperiosteal tissue in the jaws.

8. The method of claim 1, wherein said expanding is done by introducing a biocompatible filling material into said container.

9. The method of claim 8, wherein said filling material includes material for promoting the growth of bone tissue.

10. The method of claim 8, wherein said introducing is performed via a filling conduit partially protruding outside the body.

11. The method of claim 10, wherein said filling conduit is connected to said container after said inserting into the tissue.

12. The method of claim 10, wherein said container is inserted inside the body being at least partially inside said filling conduit.

13. The method of claim 8, wherein said region is perforated, having pores which are sufficiently large to allow the ingrowth of bone tissue.

14. The method of claim 13, wherein said expandable portion of said container includes an area which is less penetrable to tissue than said region.

15. The method of claim 14 wherein said area is designed to prevent the filling material from passing through said area.

16. The method of claim 14, wherein said area prevents ingrowth of tissue.

17. The method of claim 14, wherein said area is located at one side of said expandable portion of said container and said region is located at the opposite side to said expandable portion of said container.

18. The method of claim 13, wherein said expandable portion of said container is inserted between said bone and said covering tissue so as to increase the distance between said bone and said covering tissue, said covering tissue is selected from the group consisting of periosteal tissue and Schneiderian membrane, said expanding is done by introducing a biocompatible material that includes a material that promotes bone tissue regeneration into said container.

19. The method of claim 13, wherein said container includes a fixation component to prevent movements of said container.

20. The method of claim 8, further comprising, prior to inserting said expandable portion of said container, forming a path of insertion and a space for said container.

21. The method of claim 8, wherein said hole is the only aperture in the periosteal tissues of said bone through which said container is allowed at least partially to pass through.

22. The method of claim 8, wherein said expandable portion of said container being located between said bone and said periosteal tissue.

23. The method of claim 8, wherein said expanding is displacing at least part of the Schneiderian membrane so said expandable portion of said container being located completely below said part of said displaced Schneiderian membrane and said bone is the maxillary bone.

24. The method of claim 1, wherein said container includes a protruding element designed to protrude through said hole.

25. The method of claim 24, wherein said protruding element includes a sealing means for sealing said protruding element.

26. The method of claim 24, wherein said protruding element includes a hollow screw.

27. The method of claim 1, wherein said area includes at least one biocompatible material selected from the group made up of: a metal, a metal alloy, a polymer, a copolymer and ceramics.

28. The method of claim 1, wherein said area is facing the Schneiderian membrane and said expanding is displacing said Schneiderian membrane.

29. The method of claim 1, wherein said bone being touched from above by said covering tissue of said bone and from below being touched by a second covering tissue of said bone, said expandable portion of said container is being completely below said covering tissue of said bone and at least partially above said second covering tissue of said bone and inside the body for at least several days.

30. The method of claim 29, wherein said expandable portion of said container is configured to have a first portion which is not perforated and a second portion which is perforated.

31. The method of claim 29, wherein said container includes mechanical component assisting in the enlargement of said expandable portion of said container.

32. The method of claim 29, wherein said covering tissue is the Schneiderian membrane above said bone and said second covering tissue is part of the periosteal tissue of the upper jaw.

33. The method of claim 29, wherein said expandable portion of said container is inserted so at least part of said expandable portion of said container is inside said bone.

34. The method of claim 29, wherein said expandable portion of said container being completely below the displaced part of said covering tissue of said bone.

35. The method of claim 1, wherein said expanding is stretching said periosteal tissue.

36. The method of claim 1, wherein inserting the majority of said container through a hole in said bone, said hole in said bone being surrounded all around by said bone.

37. The method of claim 1, further comprising, prior to inserting said expandable portion of said container peeling said Schneiderian membrane from said bone.

38. The method of claim 36, wherein said expanding is done by introducing a biocompatible filling material into said container.

39. The method of claim 38, wherein said expandable portion of said container is at least partially located in a cavity inside said bone.

40. The method of claim 39, wherein said cavity has at least one place of non-continuity of the bone at the borders of said cavity.

41. The method of claim 40, wherein said expandable portion of said container includes an area which is less penetrable to tissue than said region, said area is facing said non-continuity.

42. The method of claim 41, wherein said area prevents the leakage of said filling material.

43. The method of claim 38, wherein said expandable portion of said container is expanded in a chamber in the body having hard bone tissue at most of the borders of said chamber and softer tissue inside said chamber.

44. The method of claim 43, wherein said introducing is displacing said softer tissue.

45. The method of claim 38, wherein said expandable portion of said container is bounded from one side by said bone surface and from another side by at least one of the soft tissues that were adjacent to said bone before starting the surgical procedure.

46. The method of claim 45, wherein, said expandable portion of said container includes an area which is less penetrable to tissue than said region, said region being placed adjacent to said bone surface and said area being placed facing at least part of said soft tissues.

47. The method of claim 46, wherein said region is a perforated region having pores which are sufficiently large to allow the ingrowth of bone tissue and said area prevents the leakage of said filling material outside said container.

48. The method of claim 38, wherein said filling material includes a first filling material and a second filling material, said container having pores to allow the release of said second filling material while preventing the release of said first filling material.

49. The method of claim 38, wherein said container allows the release of part of said filling material.

50. The method of claim 49, wherein said introducing is done so said part of said filling material is released outside said container.

51. The method of claim 50 wherein said container has pores that are sized according to the filling material to be released.

52. The method of claim 38, wherein said expandable portion of said container is inserted so that the largest diameter of said expandable portion of said container after being expanded is larger than the largest diameter of said hole in said bone.

53. The method of claim 1, wherein inserting the majority of said container through a hole in said bone, said hole in said bone being surrounded substantially all around by said bone.

54. The method of claim 1, wherein said expanding is displacing at least one of the tissues touching said expandable portion of said container from said bone surface.

55. The method of claim 1, wherein said hole in said periosteal tissue is done using a drill to create a round hole.

56. The method of claim 1, wherein inserting the majority of said container through a hole in said bone, said hole in said bone is done using a drill to create a round hole.

57. The method of claim 56, wherein said container includes a filling conduit, the dimension of said hole in said bone fits the dimension of said filling conduit so said filling conduit is touching said hole in said bone substantially all around the borders of said hole in said bone.

58. The method of claim 56, wherein said expanding is done by introducing a biocompatible filling material into said container through a rigid tube, said tube fits the size of said hole in said bone.

59. The method of claim 1, wherein said hole being surrounded all around by said periosteal tissue.

60. The method of claim 1, wherein said expandable portion of said container includes an area which prevents ingrowth of tissue and said region is perforated, having pores which are sufficiently large to allow the ingrowth of bone tissue.

61. The method of claim 1, wherein said covering tissue is the periosteal tissue covering the external surface of said bone.

62. The method of claim 61, wherein said expandable portion of said container includes an area which prevents ingrowth of epithelial tissue and said region is perforated, having pores which are sufficiently large to allow the ingrowth of bone tissue.

63. The method of claim 62, wherein at least part of said expanding is done by introducing a bone growth inducing material into said container.

64. The method of claim 62, wherein said bone is the alveolar ridge and said periosteal tissue is displaced towards the oral cavity.

65. The method of claim 64, wherein at least part of said area is made from a guided bone regeneration membrane and said guided bone regeneration membrane is facing said periosteal tissue.

66. The method of claim 65, wherein at least part of said expanding is done by introducing a bone growth inducing material into said container.

67. The method of claim 61, wherein at least part said expanding is done by introducing a bone growth inducing material into said container.

68. The method of claim 61, wherein said bone is the alveolar ridge and said periosteal tissue is displaced towards the oral cavity.

69. The method of claim 38, wherein said filling material is a bone filler.

70. The method of claim 1, wherein said covering tissue is the Schneiderian membrane and at least part of said area is made from a guided bone regeneration membrane.

* * * * *